(12) United States Patent
Yan et al.

(10) Patent No.: US 9,121,044 B2
(45) Date of Patent: Sep. 1, 2015

(54) BIOSYNTHESIS OF CAFFEIC ACID AND CAFFEIC ACID DERIVATIVES BY RECOMBINANT MICROORGANISMS

(71) Applicant: UNIVERSITY OF GEORGIA RESEARCH FOUNDATION, INC., Athens, GA (US)

(72) Inventors: Yajun Yan, Athens, GA (US); Yuheng Lin, Athens, GA (US)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 0 days.

(21) Appl. No.: 14/326,962

(22) Filed: Jul. 9, 2014

(65) Prior Publication Data

US 2015/0184205 A1    Jul. 2, 2015

Related U.S. Application Data

(62) Division of application No. 13/670,213, filed on Nov. 6, 2012, now Pat. No. 8,809,028.

(60) Provisional application No. 61/556,504, filed on Nov. 7, 2011.

(51) Int. Cl.
  *C12P 7/42* (2006.01)
  *C12N 9/88* (2006.01)
  *C12N 9/02* (2006.01)

(52) U.S. Cl.
  CPC ............... *C12P 7/42* (2013.01); *C12N 9/0071* (2013.01); *C12N 9/88* (2013.01); *C12Y 114/14009* (2013.01); *C12Y 403/01023* (2013.01)

(58) Field of Classification Search
  None
  See application file for complete search history.

(56) References Cited

U.S. PATENT DOCUMENTS

| | | |
|---|---|---|
| 2009/0011400 A1 | 1/2009 | Noel et al. |
| 2013/0130340 A1 | 5/2013 | Yan et al. |

FOREIGN PATENT DOCUMENTS

| | | |
|---|---|---|
| KR | 2009131845 | 12/2009 |

OTHER PUBLICATIONS

Berner et al., "Genes and enzymes involved in caffeic acid biosynthesis in the actinomycete *Saccharothrix espanaensis*," Apr. 2006 *J Bacteriol* 188(7):2666-2673.

Bourgaud et al., "Biosynthesis of coumarins in plants: a major pathway still to be unravelled for cytochrome P450 enzymes," Jun. 2006 *Phytochem Rev* 5:293-308.

Celik et al., "Caffeic acid phenethyl ester (CAPE) exhibits significant potential as an antidiabetic and liver-protective agent in streptozotocin-induced diabetic rats," Oct. 2009 *Pharmacol Res* 60:270-276. Available online on Apr. 7, 2009.

Chao et al., "Anti-inflammatory and anti-coagulatory activities of caffeic acid and ellagic acid in cardiac tissue of diabetic mice," Aug. 14, 2009 *Nutr Metab (Lond)* 6:33; 8 pages.

Chavez-Bejar et al., "Metabolic engineering of *Escherichia coli* for L-tyrosine production by expression of genes coding for the chorismate mutase domain of the native chorismate mutase-prephenate dehydratase and a cyclohexadienyl dehydrogenase from *Zymomonas mobilis*," May 2008 *Appl Environ Microbiol* 74:3284-3290. Available online on Mar. 14, 2008.

Choi et al., "Biosynthesis of plant-specific phenylpropanoids by construction of an artificial biosynthetic pathway in *Escherichia coli*," Oct. 1, 2011 *J Ind Microbio. Biotechnol* 38(10):1657-1665. Available online Mar. 20, 2011.

Datsenko and Wanner, "One-step inactivation of chromosomal genes in *Escherichia coli* K-12 using PCR products," Jun. 6, 2000 *Proc Natl Acad Sci USA* 97:6640-6645.

Dharmadi et al., "Anaerobic fermentation of glycerol by *Escherichia coli*: a new platform for metabolic engineering," Aug. 5, 2006 *Biotechnol Bioeng* 94:821-9. Available online on May 20, 2006.

Gerhardt et al. (eds.) *Methods for General and Molecular Bacteriology*, American Society for Microbiology, chapters 13-14 and 16-18 (1994).

Gulcin, "Antioxidant activity of caffeic acid (3,4-dihydroxycinnamic acid)," Jan. 16, 2006 *Toxicology* 217:213-220. Available online on Oct. 21, 2005.

Heckman et al., "Gene splicing and mutagenesis by PCR-driven overlap extension," Jun. 2007 *Nat Protoc* 2:924-932. Available online on Apr. 12, 2007.

Huang et al., "Biosynthesis of caffeic acid by metabolically engineered *Escherichia coli*," slides shown at an oral presentation given at the 17th Annual Conference of the Institute of Biological Engineering; Mar. 1-3, 2012: Indianapolis, IN.

Huang et al., "Caffeic acid production enhancement by engineering a phenylalanine over-producing *Escherichia coli* strain," Dec. 2013 *Biotechnol. Bioeng.* 110:3188-3196. Available online on Jul. 11, 2013.

Ikeda et al., "Inhibition of multiplication of herpes simplex virus by caffeic acid," Oct. 2011 *Int J Mol Med* 28:595-598. Available online on Jul. 1, 2011.

Kim et al., "Crystal structure of the oxygenase component (HpaB) of the 4-hydroxyphenylacetate 3-monooxygenase from *Thermus thermophilus* HB8," Nov. 9, 2007 *J Biol Chem* 282(45):33107-33117.

(Continued)

*Primary Examiner* — Suzanne M Noakes

(74) *Attorney, Agent, or Firm* — Mueting, Raasch & Gebhardt, P.A.

(57) ABSTRACT

Microorganisms are genetically engineered to synthesize caffeic acid from simple carbon sources via a tyrosine intermediate by means of a dual pathway that utilizes both endogenous and engineered enzymatic activities.

16 Claims, 6 Drawing Sheets

(56) References Cited

OTHER PUBLICATIONS

Kim et al., "Gene engineering, purification, crystallization and preliminary X-ray diffraction of cytochrome P450 p-coumarate-3-hydroxylase (C3H), the *Arabidopsis* membrane protein," Sep. 2011 *Protein Expr Purif* 79:149-155. Available online on Apr. 29, 2011.
Kneusel et al., "Formation of trans-caffeoyl-CoA from trans-4-coumaroyl-CoA by $Zn^{2+}$-dependent enzymes in cultured plant cells and its activation by an elicitor-induced pH shift," Mar. 1989 *Arch Biochem Biophys* 269:455-462.
Kojima and Takeuchi, "Detection and characterization of p-coumaric acid hydroxylase in mung bean, *Vigna mungo*, seedlings," Feb. 1989 *J Biochem* 105:265-270.
Leonard et al., "Opportunities in metabolic engineering to facilitate scalable alkaloid production," May 2009 *Nat Chem Biol* 5:292-300.
Liebgott et al., "Hydroxytyrosol from tyrosol using hydroxyphenylacetic acid-induced bacterial cultures and evidence of the role of 4-HPA 3-hydroxylase," Dec. 2009 *Res Microbiol* 160:757-766. Available online on Oct. 28, 2009.
Lin and Yan, "Biosynthesis of caffeic acid in *Escherichia coli* using its endogenous hydroxylase complex," Apr. 4, 2012 *Microb Cell Fact* 11:42; 9 pages.
Louie et al., "Coordinated production and utilization of FADH2 by NAD(P)H-flavin oxidoreductase and 4-hydroxyphenylacetate 3-monooxygenase," Jun. 24, 2003 *Biochemistry* 42:7509-7517.
Lutke-Eversloh et al., "Feedback inhibition of chorismate mutase/prephenate dehydrogenase (TyrA) of *Escherichia coli*: generation and characterization of tyrosine-insensitive mutants," Nov. 2005 *Appl Environ Microbiol* 71:7224-7228.
Lutke-Eversloh and Stephanopoulos, "L-tyrosine production by deregulated strains of *Escherichia coli*," May 2007 *Appl Microbiol Biotechnol* 75:103-110. Available online on Jan. 13, 2007.
Lutz and Bujard, "Independent and tight regulation of transcriptional units in *Escherichia coli* via the LacR/O, the TetR/O and AraC/I1-I2 regulatory elements," Mar. 15, 1997 *Nucleic Acids Res* 25:1203-1210.
Mori et al., "Antioxidant Activity of Caffeic Acid through a Novel Mechanism under UVA Irradiation," Jul. 2009 *J Clin Biochem Nutr* 45:49-55. Available online on Jun. 30, 2009.
Munoz et al., "Metabolic engineering of *Escherichia coli* for improving L-3,4-dihydroxyphenylalanine (L-DOPA) synthesis from glucose," Nov. 2011 *J Ind Microbiol Biotechnol* 38:1845-1852. Available online on Apr. 22, 2011.
Nakagawa et al., "A bacterial platform for fermentative production of plant alkaloids," May 24, 2011 *Nat Commun* 2:326; 9 pages.
Olson et al., "Production of tyrosine from sucrose or glucose achieved by rapid genetic changes to phenylalanine-producing *Escherichia coli* strains," Apr. 2007 *Appl Microbiol Biotechnol* 74(5):1031-40.
Omene et al., "Caffeic Acid Phenethyl Ester (CAPE) derived from propolis, a honeybee product, inhibits growth of breast cancer stem cells," Aug. 2012 *Invest New Drugs* 30:1279-1288. Available online on May 3, 2011.
Phongsak et al., "The C-terminal domain of 4-hydroxyphenylacetate 3-hydroxylase from *Acinetobacter baumannii* is an autoinhibitory domain," Jul. 27, 2012 *J. Biol. Chem.* 287:26213-26222. Available online on Jun. 3, 2012.

Prieto et al., "Characterization of an *Escherichia coli* aromatic hydroxylase with a broad substrate range," Apr. 1993 *J Bacteriol* 175:2162-2167.
Rajendra-Prasad et al., "Inhibitory effect of caffeic acid on cancer cell proliferation by oxidative mechanism in human HT-1080 fibrosarcoma cell line," Mar. 2011 *Mol Cell Biochem* 349:11-19. Available online on Nov. 30, 2010.
Sachan et al., "Co-production of caffeic acid and p-hydroxybenzoic acid from p-coumaric acid by *Streptomyces caeruleus* MTCC 6638," Aug. 7, 2006 *Appl Microbiol Biotechnol* 71:720-727. Available online on Nov. 16, 2005.
Sambrook et al., *Molecular cloning: a laboratory manual. $2^{nd}$ edition* NY: Cold Spring Harbor Laboratory; 1989.
Santos et al., "Optimization of a heterologous pathway for the production of flavonoids from glucose," Jul. 2011 *Metab Eng* 13:392-400. Available online on Feb. 12, 2011.
Shen and Liao, "Metabolic engineering of *Escherichia coli* for 1-butanol and 1-propanol production via the keto-acid pathways," Nov. 2008 *Metab Eng* 10:312-320. Available online on Aug. 17, 2008.
Smetanska, "Production of secondary metabolites using plant cell cultures," 2008 *Adv Biochem Eng Biotechno* 111:187-228.
Wang et al., "Application of response surface methodology optimization for the production of caffeic acid from tobacco waste," Apr. 20, 2009 *Af J Biotechnol* 8:1416-1424.
Wu et al., "Caffeic acid phenethyl ester (CAPE), derived from a honeybee product propolis, exhibits a diversity of anti-tumor effects in pre-clinical models of human breast cancer," Sep. 1, 2011 *Cancer Lett* 308:43-53. Available online on May 13, 2011.
Xue et al., "Identification, characterization and functional expression of a tyrosine ammonia-lyase and its mutants from the photosynthetic bacterium *Rhodobacter sphaeroides*," Sep. 2007 *J Ind Microbiol Biotechnol* 34:599-604. Available online on Jun. 30, 2007.
Xun et al., "Characterization of 4-hydroxyphenylacetate 3-hydroxylase (HpaB) of *Escherichia coli* as a reduced flavin adenine dinucleotide-utilizing monooxygenase," Feb. 2000 *Appl Environ Microbiol* 66(2):481-486.
Yan et al., "Metabolic engineering of anthocyanin biosynthesis in *Escherichia coli*," Jul. 2005 *Appl Environ Microbiol* 71:3617-3623.
Yan et al., "Biosynthesis of natural flavanones in *Saccharomyces cerevisiae*," Sep. 2005 *Appl Environ Microbiol* 71:5610-5613.
Yan et al., "Biosynthesis of 5-deoxyflavanones in microorganisms," Oct. 2007 *Biotechnol J* 2:1250-1262.
Yan et al., "High-yield anthocyanin biosynthesis in engineered *Escherichia coli*," May 1, 2008 *Biotechnol Bioeng* 100:126-140.
Yoshimoto et al., "Enzymatic production of caffeic acid by koji from plant resources containing caffeoylquinic acid derivatives," Sep. 2005 *Biosci Biotechnol Biochem* 69:1777-1781.
Zrelli et al., "Hydroxytyrosol reduces intracellular reactive oxygen species levels in vascular endothelial cells by upregulating catalase expression through the AMPK-FOXO3a pathway," Jun. 25, 2011 *Eur J Pharmacol* 660:275-82. Available online on Apr. 12, 2011.
U.S. Appl. No. 13/670,213; Request for Restriction/Election issued Oct. 10, 2013; 8 pages.
U.S. Appl. No. 13/670,213; Office Action issued Nov. 29, 2013; 9 pages.

```
                        SEQUENCE LISTING

<160> NUMBER OF SEQ ID NOS: 22

<210> SEQ ID NO 1
<211> LENGTH: 32
<212> TYPE: DNA
<213> ORGANISM: artificial
<220> FEATURE:
<223> OTHER INFORMATION: synthetic oligonucleotide primer

<400> SEQUENCE: 1
gggaaaggta ccatgctcga tgcaaccatc gg                               32

<210> SEQ ID NO 2
<211> LENGTH: 30
<212> TYPE: DNA
<213> ORGANISM: artificial
<220> FEATURE:
<223> OTHER INFORMATION: synthetic oligonucleotide primer

<400> SEQUENCE: 2
gggaaagcat gctcatgccg ggggatcggc                                  30

<210> SEQ ID NO 3
<211> LENGTH: 29
<212> TYPE: DNA
<213> ORGANISM: artificial
<220> FEATURE:
<223> OTHER INFORMATION: synthetic oligonucleotide primer

<400> SEQUENCE: 3
gggaaaggta ccatgctcgc catgagccc                                   29

<210> SEQ ID NO 4
<211> LENGTH: 34
<212> TYPE: DNA
<213> ORGANISM: artificial
<220> FEATURE:
<223> OTHER INFORMATION: synthetic oligonucleotide primer

<400> SEQUENCE: 4
gggaaagcat gctcagacgg gagattgctg caag                             34

<210> SEQ ID NO 5
<211> LENGTH: 35
<212> TYPE: DNA
<213> ORGANISM: artificial
```

```
<220> FEATURE:
<223> OTHER INFORMATION: synthetic oligonucleotide primer

<400> SEQUENCE: 5
gggaaaggta ccatgaaacc agaagatttc cgcgc                              35

<210> SEQ ID NO 6
<211> LENGTH: 37
<212> TYPE: DNA
<213> ORGANISM: artificial
<220> FEATURE:
<223> OTHER INFORMATION: synthetic oligonucleotide primer

<400> SEQUENCE: 6
gggaaagcat gcttaaatcg cagcttccat ttccagc                            37

<210> SEQ ID NO 7
<211> LENGTH: 50
<212> TYPE: DNA
<213> ORGANISM: artificial
<220> FEATURE:
<223> OTHER INFORMATION: synthetic oligonucleotide primer

<400> SEQUENCE: 7
gggaaagcat gcaggagata taccatgaaa ccagaagatt tccgcgccag              50

<210> SEQ ID NO 8
<211> LENGTH: 40
<212> TYPE: DNA
<213> ORGANISM: artificial
<220> FEATURE:
<223> OTHER INFORMATION: synthetic oligonucleotide primer

<400> SEQUENCE: 8
gggaaatcta gattaaatcg cagcttccat ttccagcatc                         40

<210> SEQ ID NO 9
<211> LENGTH: 32
<212> TYPE: DNA
<213> ORGANISM: artificial
<220> FEATURE:
<223> OTHER INFORMATION: synthetic oligonucleotide primer

<400> SEQUENCE: 9
gcgcgaggca tctattttgg cctcgcgtcg tg                                 32

<210> SEQ ID NO 10
<211> LENGTH: 32
<212> TYPE: DNA
<213> ORGANISM: artificial
<220> FEATURE:
<223> OTHER INFORMATION: synthetic oligonucleotide primer

<400> SEQUENCE: 10
cacgacgcga ggccaaaata gatgcctcgc gc                                 32

<210> SEQ ID NO 11
<211> LENGTH: 35
<212> TYPE: DNA
<213> ORGANISM: artificial
<220> FEATURE:
<223> OTHER INFORMATION: synthetic oligonucleotide primer

<400> SEQUENCE: 11
ctggttcggc gattacgtgc agcgttttca gagtg                              35
```

<210> SEQ ID NO 12
<211> LENGTH: 35
<212> TYPE: DNA
<213> ORGANISM: artificial
<220> FEATURE:
<223> OTHER INFORMATION: synthetic oligonucleotide primer

<400> SEQUENCE: 12
cactctgaaa acgctgcacg taatcgccga accag                           35

<210> SEQ ID NO 13
<211> LENGTH: 31
<212> TYPE: DNA
<213> ORGANISM: artificial
<220> FEATURE:
<223> OTHER INFORMATION: synthetic oligonucleotide primer

<400> SEQUENCE: 13
gcaggtgagt tctcaacat gatcaccca c                                 31

<210> SEQ ID NO 14
<211> LENGTH: 31
<212> TYPE: DNA
<213> ORGANISM: artificial
<220> FEATURE:
<223> OTHER INFORMATION: synthetic oligonucleotide primer

<400> SEQUENCE: 14
gtggggtgat catgttgaga aactcacctg c                               31

<210> SEQ ID NO 15
<211> LENGTH: 38
<212> TYPE: DNA
<213> ORGANISM: artificial
<220> FEATURE:
<223> OTHER INFORMATION: synthetic oligonucleotide primer

<400> SEQUENCE: 15
gggaaaggta ccatggttgc tgaattgacc gcattacg                        38

<210> SEQ ID NO 16
<211> LENGTH: 45
<212> TYPE: DNA
<213> ORGANISM: artificial
<220> FEATURE:
<223> OTHER INFORMATION: synthetic oligonucleotide primer

<400> SEQUENCE: 16
gggaaagtcg acgcatatgt tactggcgat tgtcattcgc ctgac                45

<210> SEQ ID NO 17
<211> LENGTH: 46
<212> TYPE: DNA
<213> ORGANISM: artificial
<220> FEATURE:
<223> OTHER INFORMATION: synthetic oligonucleotide primer

<400> SEQUENCE: 17
gggaaacata tgaggagata taccatgtcc aacaatggct cgtcac                46

<210> SEQ ID NO 18
<211> LENGTH: 40
<212> TYPE: DNA
<213> ORGANISM: artificial
<220> FEATURE:
<223> OTHER INFORMATION: synthetic oligonucleotide primer

```
<400> SEQUENCE: 18
gggaaagtcg acttatttct tcagttcagc caggcttaac                    40

<210> SEQ ID NO 19
<211> LENGTH: 48
<212> TYPE: DNA
<213> ORGANISM: artificial
<220> FEATURE:
<223> OTHER INFORMATION: synthetic oligonucleotide primer

<400> SEQUENCE: 19
gggaaactcg agaggagata taccatgtcc tcacgtaaag agcttgcc            48

<210> SEQ ID NO 20
<211> LENGTH: 39
<212> TYPE: DNA
<213> ORGANISM: artificial
<220> FEATURE:
<223> OTHER INFORMATION: synthetic oligonucleotide primer

<400> SEQUENCE: 20
gggaaagcat gcttacagca gttctttgc tttcgcaac                      39

<210> SEQ ID NO 21
<211> LENGTH: 51
<212> TYPE: DNA
<213> ORGANISM: artificial
<220> FEATURE:
<223> OTHER INFORMATION: synthetic oligonucleotide primer

<400> SEQUENCE: 21
gggaaagcat gcaggagata taccatgaat tatcagaacg acgatttacg c        51

<210> SEQ ID NO 22
<211> LENGTH: 33
<212> TYPE: DNA
<213> ORGANISM: artificial
<220> FEATURE:
<223> OTHER INFORMATION: synthetic oligonucleotide primer

<400> SEQUENCE: 22
gggaaaaagc ttttacccgc gacgcgcttt tac                           33
```

US 9,121,044 B2

BIOSYNTHESIS OF CAFFEIC ACID AND CAFFEIC ACID DERIVATIVES BY RECOMBINANT MICROORGANISMS

CONTINUING APPLICATION DATA

This application is a division of U.S. Ser. No. 13/670,213, filed Nov. 6, 2012, which claims the benefit of U.S. Provisional Application Ser. No. 61/556,504, filed Nov. 7, 2011, each of which is incorporated by reference herein.

This application contains a Sequence Listing electronically submitted via EFS-Web to the United States Patent and Trademark Office as an ASCII text filed entitled "235.01950102_SequenceListing_ST25" having a size of 5 kilobytes and created on Jul. 1, 2014. Due to the electronic filing of the Sequence Listing, the electronically submitted Sequence Listing serves as both the paper copy required by 37 CFR §1.821(c) and the CRF required by §1.821(e). The information contained in the Sequence Listing is incorporated by reference herein.

BACKGROUND

Caffeic acid (3,4-dihydroxycinnamic acid) is a natural phenolic compound found in plants. Previous studies on its biological activities suggested that caffeic acid possesses antioxidant (Mori et al., J Clin Biochem Nutr 2009, 45:49-55; Gulcin, Toxicology 2006, 217:213-220), anti-virus (Ikeda et al., Int J Mol Med 2011, 28:595-598), anti-cancer (Rajendra-Prasad et al., Mol Cell Biochem 2011, 349:11-19) and anti-inflammatory properties (Chao et al., Nutr Metab (Lond) 2009, 6:33). Moreover, its derivative, caffeic acid phenethyl ester (CAPE), has drawn great attention because of its demonstrated therapeutic effects including its potential as an anti-diabetic and liver-protective agent as well as an anti-tumor drug for human breast cancer treatment (Wu et al., Cancer Lett 2011, 308:43-53; Celik et al., Pharmacol Res 2009, 60:270-276).

Caffeic acid is one of the pivotal intermediates of plant phenylpropanoid pathway starting from the deamination of phenylalanine which generates cinnamic acid. Followed by a two-step sequential hydroxylation at the 4- and 3-position of the benzyl ring, cinnamic acid is converted into caffeic acid via p-coumaric acid (FIG. 1; Bourgaud et al., Phytochem Rev 2006, 5:293-308; Kojima and Takeuchi, J Biochem 1989, 105:265-270). The involved enzymes, cinnamate 4-hydroxylase (C4H) and p-coumarate 3-hydroxylase (C3H) are plant-specific cytochrome P450 dependent monooxygenases. Due to their instability and membrane-bound property, the purification and characterization of these enzymes are quite challenging, particularly for C3H (Kim et al., Protein Expr Purif 2011, 79:149-155). It was also suggested that the hydroxylation at the 3-position could also occur after p-coumaric acid is esterified, which does not generate caffeic acid as the intermediate (Bourgaud et al., Phytochem Rev 2006, 5:293-308; Kneusel et al., Arch Biochem Biophys 1989, 269:455-462). Recently, genes and enzymes involved in caffeic acid biosynthesis were also reported in the actinomycete *Saccharothrix espanaensis*. A tyrosine ammonia lyase (TAL) encoded by sam8 and a microbial C3H encoded by sam5 are responsible for the conversion of tyrosine to p-coumaric acid and then to caffeic acid, respectively (Berner et al., J Bacteriol 2006, 188:2666-2673).

Currently, caffeic acid is produced by extraction from plant sources, such as coffee beans. Chemical or enzymatic hydrolysis of caffeoylquinic acid derivatives is also employed to produce caffeic acid (Wang et al., AfJ Biotechnol 2009, 8:1416-1424; Yoshimoto et al., Biosci Biotechnol Biochem 2005, 69:1777-1781). Like many other secondary metabolites, caffeic acid derivatives are usually accumulated at low levels in plants and hence the isolation of these compounds is to some extent difficult and expensive.

Over the past few decades, advances in metabolic engineering and synthetic biology have enabled the production of various plant-specific secondary metabolites in recombinant microorganisms (Yan et al., Appl Environ Microbiol 2005, 71:3617-3623; Yan et al., Appl Environ Microbiol 2005, 71:5610-5613; Yan et al., Biotechnol J 2007, 2:1250-1262; Yan et al., Biotechnol Bioeng 2008, 100:126-140). Microbial systems have been explored by some researchers as an alternative to extraction for caffeic acid production. Sachan et al. reported the co-production of caffeic acid and p-hydroxybenzoic acid in *Streptomyces caeruleus* using p-coumaric acid as the carbon source (Appl Microbiol Biotechnol 2006, 71:720-727). More recently, the conversion of tyrosine to caffeic acid (the titer was not reported) and ferulic acid (7.1 mg/L) in *E. coli* was achieved by the co-expression of the enzymes encoded by the sam5 and sam8 from *S. espanaensis* and an O-methyltransferase from *Arabidopsis thaliana* (Choi et al., J Ind Microbiol Biotechnol 2011, 38:1657-1665). However, the above-mentioned studies relied on feeding the direct precursors such as tyrosine and p-coumaric acid, which would increase the production cost and cannot be preferred for large-scale production.

SUMMARY OF THE INVENTION

The present invention provides microbial cells that are metabolically engineered for production of caffeic acid, as well methods for making said cells and methods for producing and isolating caffeic acid and, optionally, its derivatives and downstream metabolites, from said cells or cell culture.

In one aspect, the invention provides a genetically engineered cell having p-coumarate 3-hydroxylase (C3H) enzyme activity, which has been metabolically engineered to express or overexpress a tyrosine ammonia lyase (TAL). Preferably, the p-coumarate 3-hydroxylase activity is provided by an endogenous 4-hydroxyphenylacetate 3-hydroxylase (4HPA3H) enzyme or enzyme complex. Optionally, the genetically engineered cell may be further metabolically engineered to also overexpress a 4HPA3H enzyme or enzyme complex. Preferably, the genetically engineered cell has a metabolic pathway for the biosynthesis of tyrosine. Optionally the genetically engineered cell has been further metabolically engineered to overproduce tyrosine compared to a wild-type cell. A genetically engineered cell of the invention which overproduces tyrosine may have reduced or eliminated feedback inhibition of tyrosine biosynthesis and/or have carbon flow which has been redirected toward tyrosine biosynthesis. Preferably, the genetically engineered cell of the invention is a bacterial cell. More preferably, the genetically engineered cell is an *Escherichia coli* cell.

The genetically engineered cell optionally includes at least one vector operably encoding a TAL. The genetically engineered cell may also include at least one vector operably encoding an enzyme having C3H activity. In one embodiment, a single vector encodes both the TAL and the enzyme having C3H activity. In another embodiment, the genetically engineered cell includes a first vector encoding the TAL and a second vector encoding the enzyme having C3H activity.

The invention also provides a method for making a genetically engineered cell. The method can include introducing a first polynucleotide encoding a TAL and a second polynucleotide encoding an enzyme having C3H activity into a host cell such that the resulting genetically engineered cell overexpresses a TAL and overexpresses an enzyme having C3H activity. The host cell may or may not possess endogenous TAL and/or C3H enzyme activity. The first and second polynucleotides may be positioned on a single vector. Alternatively, the first and second polynucleotides may be positioned on different vectors. The cell may overproduce tyrosine compared to a wild-type cell. Preferably the cell is a bacterial cell. More preferably the bacterial cell is an *E. coli* cell.

In another aspect, the invention provides a method for producing caffeic acid. The method includes culturing a genetically engineered cell which overexpresses a TAL and an enzyme having C3H activity under conditions effective to produce caffeic acid and isolating the caffeic acid from the cell or the culture medium. The method may also include supplying at least one carbon source such as glycerol, glucose, gluconate, acetate, xylose, sucrose, arabinose, mannose, etc. The cell can be a bacterial cell, preferably an *E. coli* cell. The culturing step may be performed under either aerobic or anaerobic conditions.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
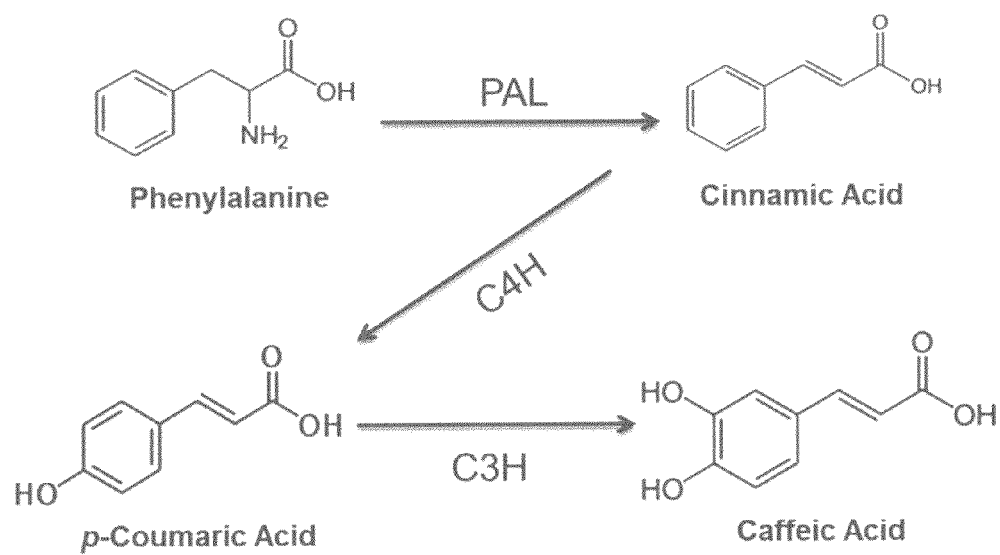
FIG. 1 shows the native plant pathway for alkaline hydrolysis of caffeoylquinic acids. Enzymes shown include phenylalanine ammonia lyase (PAL), cinnamate 4-hydroxylase (C4H), and p-coumarate 3-hydroxylase (C3H).

Caffeic acid is synthesized in plants via a metabolic pathway that utilizes phenylalanine as a starting material. Phenylalanine is deaminated through the action of phenylalanine ammonia lyase (PAL) to yield cinnamic acid. Cinnamic acid is hydroxylated at the 4-position of the benzyl ring through the action of cinnamate 4-hydroxylase (C4H) to yield the intermediate p-coumaric acid, which is then hydroxylated at the 3-position through the action of and p-coumarate 3-hydroxylase (C3H) to yield caffeic acid. See FIG. 1.

Extraction of caffeic acid from plant material is time consuming and inefficient, but until now there was no way to successfully and economically produce caffeic acid in a microbial system. Reconstructing plant pathways in microbial systems has proven problematic due to the lack of availability of functional enzymes that are compatible with the specific microorganism. C4H and C3H, for example, are both cytochrome P450-dependent monooxygenases that, in plants, are bound to the endoplasmic recticulum. Because these membrane-associated enzymes are not very soluble, they are difficult to express in microbial systems.

In plants, as noted above, C4H catalyzes the conversion of phenylalanine to cinnamic acid. In the present invention, however, this step in the biosynthesis of caffeic acid is circumvented by utilizing a different upstream metabolite. Instead of phenylalanine, the novel metabolic pathway of the invention proceeds from tyrosine. Relying on tyrosine rather than phenylalanine as the upstream metabolite confers several advantages to the microbial system. First, the enzyme phenylalanine ammonia lyase is not needed; rather, what is needed is an enzyme that deaminates tyrosine. Conveniently, such enzymes, termed tyrosine ammonia lyases (TALs; e.g., EC 4.3.1.23), are known and can be readily introduced into microbial systems. In our initial demonstration of this pathway, we used TALs from the genus *Rhodobacter* (more particularly, *Rhodobacter capsulatus* and *Rhodobacter sphaeroides*), but any enzyme with tyrosine ammonia lyase activity can be used. Examples of additional organisms that are known to express tyrosine ammonia lyases include *Camellia sinensis, Fragaria* x *ananassa, Ralstonia metallidurans*, and *Zea mays*. It should be understood that any enzyme with aromatic amino acid lyase activity (e.g., phenylalanine ammonia lyase, histidine ammonia lyase, tyrosine 2,3-aminomutase, or tyrosine ammonia lyase) which has sufficient tyrosine amino lyase activity in vivo, can be used. Since TALs catalyze the direct formation of p-coumaric acid from tyrosine, they bypass the enzymatic step catalyzed in the plant by C4H and it is therefore not necessary to introduce C4H activity into the engineered microbial pathway.

In the microbial system of the invention, therefore, tyrosine is converted directly into p-coumaric acid via the action of the tyrosine ammonia lyase (TAL) that has been engineered into the metabolic pathway. Yet this intermediate, p-coumaric acid, must nevertheless be hydroxylated at the 3-position on the benzyl ring in order to produce caffeic acid, so the need for C3H activity remained. This presented one of the most challenging obstacles encountered, because all C3Hs identified in plants are membrane-bound cytochrome P450-dependent monooxygenases and difficult to express in microbial systems. Additionally, although an alternative microbial C3H was identified from *S. espanaensis*, its activity seems to be low, which limits its applications (Choi et al., J Ind Microbiol Biotechnol 2011, 38:1657-1665).

This problem is solved in the present invention by making creative use of an enzyme complex that is endogenously present in *E. coli*, namely, 4-hydroxyphenylacetate 3-hydroxylase (4HPA3H). This enzyme complex can accept a broad range of substrates, three of which include 4-hydroxyphenylacetic acid (4-HPA), L-tyrosine and 4-tyrosol. Using in vitro studies, we discovered that 4HPA3H was also able to catalyze the conversion of p-coumaric acid to caffeic acid, thereby completing the pathway. To our knowledge, this is the first report of 4HPA3H enzymatic activity using p-coumaric acid as a substrate. And, because it is native to *E. coli*, this enzyme complex is expected to be compatible with a wide variety of microbial systems. However, it was discovered that wild-type *E. coli* under ordinary conditions apparently does not produce this enzyme complex, or does not produce detectable levels of this enzyme complex. Thus, in order to complete the caffeic acid biosynthetic pathway of the invention, it may be necessary to introduce 4HPA3H into the system and express or overexpress it. In wild-type *E. coli*, it was found that overexpression of hpaBC is necessary to obtain adequate 4HPA3H activity. Conveniently, introduction of 4HPA3H into the microbe can be accomplished using any type of extrachromosomal element such as a plasmid, preferably a high copy number plasmid, cosmid, DNA or RNA segment, or the like, that expresses the genes which encode the proteins that make up the 4HPA3H complex. Alternatively, genes that express the 4HPA3H enzyme complex can be chromosomally integrated. Expression of the 4HPA3H enzyme complex can be constitutive or it can be controllable or regulable, in a manner that can be turned on or off biochemically, or with heat, etc. It should be noted that in microorganisms other than *E. coli* that express sufficient 4HPA3H activity endogenously, it may not be necessary to overexpress 4HPA3H in order to obtain the desired production of caffeic acid.

A microbial metabolic pathway that converts tyrosine to caffeic acid via the action of (a) a tyrosine ammonia lyase (TAL) and (b) p-coumarate 3-hydroxylase activity in the form of a 4-hydroxyphenylacetate 3-hydroxylase (4HPA3H) provides some unexpected additional and highly significant benefits. It was surprisingly discovered that, in addition to catalyzing the 3-hydroxylation of p-coumaric acid to yield caffeic acid, 4HPA3H also catalyzed the conversion of tyrosine to an L-dopa intermediate. In other words, *E. coli* 4-hydroxyphenlacetate 3-hydroxylase (4HPA3H) was capable of hydroxylating both p-coumaric acid and tyrosine in addition to its native substrate 4-hydroxyphenylacetic acid. Moreover, the production of L-dopa was not an unwelcome diversion of carbon into a nonproductive pathway; to the contrary, it was discovered that the L-dopa intermediate could, in turn, also be converted in the caffeic acid, via the action of the TAL! For example, as shown in Example I, tyrosine ammonia lyases from *Rhodobacter* spp. were able to accept both tyrosine and L-dopa as substrates. Therefore, as can be seen in FIG. 2B, introduction of TAL and overexpression of 4HPA3H surprisingly produced a dual (parallel) metabolic pathway leading from tyrosine to caffeic acid. The two pathways utilize the two enzymes in the opposite order, thereby proceeding through two different intermediates (p-coumaric acid or L-dopa) to end up at the same final product, caffeic acid. It should be understood that in some organisms, only one of the two pathways will operate to synthesize caffeic acid from the precursor tyrosine. Cells with either one or two functional pathways (i.e., the pathway that proceeds through p-coumaric acid, the pathway that proceeds through L-dopa, or both, as shown for example in FIG. 2B) are all encompassed by the invention.

Another important advantage derives from the use of tyrosine, not phenylalanine as in plants, as the "starting material" in the microbial biosynthesis of caffeic acid. *E. coli* and other microbes biosynthesize tyrosine, so tyrosine does not have to be supplied exogenously. And, although tyrosine biosynthesis in wild-type *E. coli* is strictly controlled by several regulatory mechanisms, many strains that overproduce tyrosine have been constructed and are expected to be excellent hosts for the metabolic pathway of the invention. In Example I we show the construction of several representative strains that overproduce tyrosine, but many more are available. Bacterial tyrosine overproducers are well-known to the specialty chemical field and are in common use. Additionally, tyrosine is the starting point for the synthesis of many biochemicals. By starting with tyrosine, which is biosynthesized by the microbe from simpler carbon sources such as glucose, glycerol, gluconate, acetate and the like, the metabolic pathway of the invention avoids the need for "feeding" of a carbon intermediate (such as phenylalanine) to the culture in order to provide carbon flow to caffeic acid. It can accordingly be termed a "de novo" synthesis of caffeic acid. This important advantage substantially reduces the cost of production and allows for the use of a wide variety of microbial strains as hosts for the pathway. Any microbe that produces tyrosine can be engineered according to the invention to produce caffeic acid. In addition to the tyrosine overproducers generated in this study, any of the strains currently employed to produce tyrosine in the amino acid industry are suitable as hosts for caffeic acid production. And, even if the microorganism does not biosynthesize tyrosine, tyrosine could, if desired, be supplied in the culture medium to provide the required intermediate. With proper process optimization, industrially relevant production can be achieved.

The present invention thus provides microbial cells that are metabolically engineered for production of caffeic acid, as well methods for making said cells and methods for producing and isolating caffeic acid and, optionally, its derivatives and downstream metabolites, from said cells or cell culture. The microbial cells are preferably yeast or bacterial cells, more preferably bacterial cells. *E. coli* is an exemplary illustrative organism for the production of caffeic acid, but the invention is not intended to be limited to embodiments that utilize *E. coli*. Examples of microbial cells that can be engineered to express the caffeic acid biosynthesis pathway as described herein in addition to *E. coli*, include a wide variety of bacteria and yeast including members of the genera *Escherichia, Salmonella, Clostridium, Zymomonas, Pseudomonas, Bacillus, Rhodococcus, Alcaligenes, Klebsiella, Paenibacillus, Lactobacillus, Enterococcus, Arthrobacter, Brevibacterium, Corynebacterium Candida, Hansenula, Pichia* and *Saccharomyces*. Particularly preferred hosts include: *Escherichia coli, Bacillus subtilis Bacillus licheniformis, Alcaligenes eutrophus, Rhodococcus erythropolis, Paenibacillus macerans, Pseudomonas putida, Enterococcus faecium, Saccharomyces cerevisiae, Lactobacillus plantarum, Enterococcus gallinarium* and *Enterococcus faecalis*.

The microbial cells are metabolically engineered to extend and exploit the native tyrosine biosynthesis machinery of the organism to synthesize caffeic acid from the precursor tyrosine by means of at least one, but preferably parallel or dual metabolic pathways. Furthermore, the cells of the invention are engineered to allow caffeic acid to be synthesized from simple carbon sources.

Biosynthetic Pathway

In the native plant pathway, caffeic acid p-coumaric acid is derived from the precursor phenylalanine. This plant pathway includes at least three steps, a schematic of which is shown in FIG. 1. In the first step, deamination of phenylalanine is catalyzed by the phenylalanine ammonia lyase (PAL) enzyme to generate cinnamic acid. This is followed by a two-part sequential hydroxylation. In the second step, hydroxylation of cinnamic acid at the 4-position of the benzyl ring is catalyzed by C4H to generate p-coumaric acid. In the third step, hydroxylation of p-coumaric acid at the 3-position of the benzyl ring is catalyzed by C3H to generate caffeic acid.

Certain enzymes involved in the plant biosynthetic pathway for caffeic acid, such as p-coumarate 3-hydroxylase (C3H) and cinnamate 4-hydroxylase (C4H), are membrane bound, and expressing them in microorganisms via standard engineering techniques is problematic. Thus, identification of microbial enzymes capable of catalyzing the biosynthesis of caffeic acid will circumvent the need to attempt to express these enzymes a metabolically engineered microorganism.

Ammonia Lyase.

The novel microbial pathway of the instant invention includes an enzyme having ammonia lyase activity. The ammonia lyase is not limited to any specific ammonia lyase. The term "ammonia lyase" means a molecule that has ammonia lyase activity; i.e., that is able to catalyze deamination of a precursor molecule, such as an amino acid, to yield a deaminated intermediate. In the present invention, the deaminated intermediate is ultimately converted to caffeic acid. In a preferred embodiment, the precursor is tyrosine and the ammonia lyase is tyrosine ammonia lyase which catalyzes the production of the intermediate p-coumaric acid. The term ammonia lyase includes naturally occurring ammonia lyase enzymes together with fragments, derivatives, or any modification thereof, including enzymes encoded by insertion, deletion, or mutation of naturally occurring ammonia lyase enzymes, provided the ammonia lyase activity is retained. The precursor of the instant invention may be any aromatic compound which can be derivatized, indirectly or directly, to p-coumaric acid via an ammonia lyase. Preferably, the amino acid precursor is tyrosine. The ammonia lyase of the novel pathway can be either endogenous or heterologous. A "heterologous" enzyme is one that is encoded by a nucleotide sequence that is not normally present in the cell and is discussed in more detail below. A bacterial cell that has been transformed with and expresses a nucleotide sequences from a different species or genus that encodes an ammonia lyase expresses a heterologous enzyme.

In a preferred embodiment, the novel pathway of the invention includes a tyrosine ammonia lyase (TAL) which catalyzes deamination of tyrosine into p-coumaric acid. Exemplary TALs include, without limitation, TALs from the genus *Rhodobacter* or the *Saccharothrix espanaensis* TAL encoded by the sam8 gene. Preferably the TAL is a *R. capsulatus* or a *R. sphaeroides* TAL. More preferably, the TAL is a *R. capsulatus* TAL. Other TALs include, without limitation, TALs from *Camellia sinensis, Fragaria x ananassa, Ralstonia metallidurans*, and *Zea mays*.

Advantageously, the deamination of tyrosine results in the production of p-coumaric acid in a single step which is catalyzed by TAL.

Hydroxylase.

Figure 3:
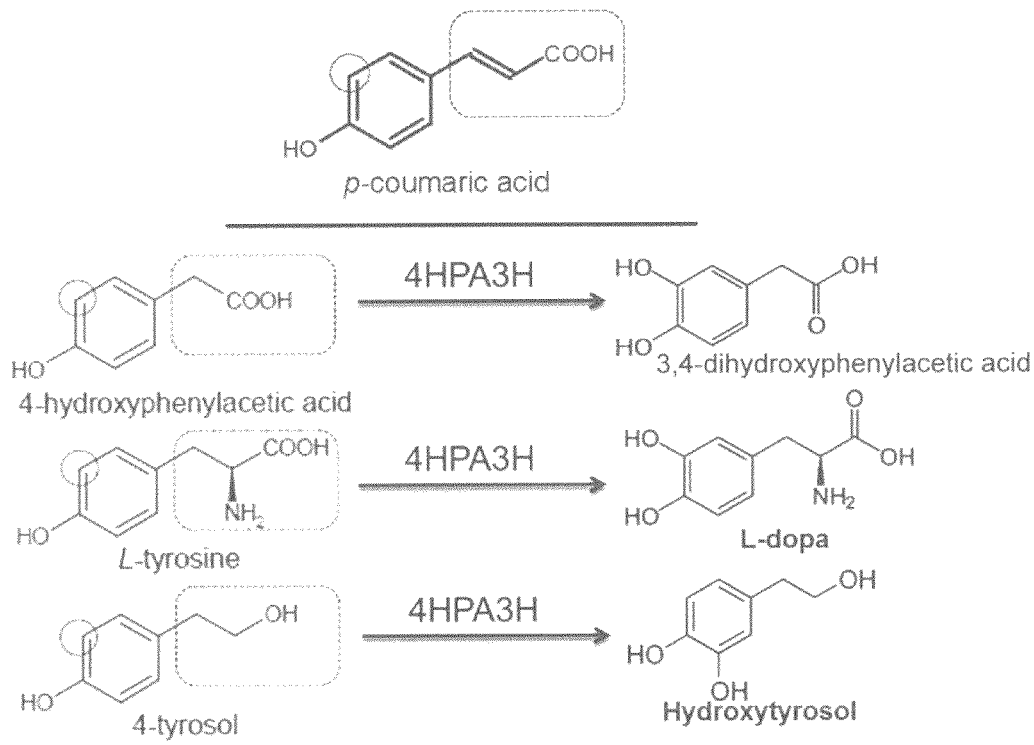
FIG. 3 shows the molecular structures of p-coumaric acid and three known substrates of 4HPA3H. The circles indicate the hydroxylation positions. The boxes indicate the difference in molecular structures.

In the plant pathway, C3H catalyzes the conversion of p-coumaric acid to caffeic acid. Microbial pathways exist which are also capable of hydroxylating aromatic compounds that have structural similarity to p-coumaric acid. Aromatic compounds having structural similarity to p-coumaric acid are shown in FIG. 3 and include 4-hydroxyphenylacetic acid (4-HPA), L-tyrosine, and 4-tyrosol. The *Escherichia coli* native enzyme 4-hydroxyphenlacetate 3-hydroxylase (4HPA3H) catalyzes the native *E. coli* substrate 4-HPA to yield 3,4-dihydroxyphenylacetic acid. Therefore, native microbial pathways relating to the metabolism of 4-HPA, tyrosine and 4-tyrosol aromatic compounds, including the *E. coli* 4HPA3H pathway, were examined. Surprisingly, it was discovered that 4HPA3H could efficiently catalyze the conversion of its nonnative substrate, p-coumaric acid, to caffeic acid. The discovery of a microbial enzyme having C3H activity, which is not membrane bound, is notable because the microbial enzyme can easily be expressed in a metabolically engineered microorganism.

Therefore, the novel pathway of the instant invention also includes a microbial enzyme having C3H activity. The term "C3H activity" means p-coumarate 3-hydroxylase activity; that is, capable of catalysing the conversion of p-coumaric acid to caffeic acid. For example, *E. coli* 4HPA3H is an enzyme that we have shown herein to have "C3H activity." Thus the term C3H activity encompasses naturally occurring C3H enzymes together with fragments, derivatives, or any modification thereof, including enzymes encoded by insertion, deletion, or mutation of naturally occurring C3H enzymes, provided the C3H activity is retained. The enzyme having C3H activity can be either endogenous or heterologous. Examples of microbial enzymes having C3H activity include the enzyme encoded by the sam5 gene of *S. espanaensis* and the 4HPA3H complex encoded by the hpaBC operon in *E. coli*, without limitation.

It should be noted that even if an enzyme is endogenous to the host organism, it may need to be overexpressed in order to provide a functional metabolic pathway. For example, the enzyme complex 4HPA3H, while endogenous to *E. coli*, does not appear to be expressed in *E. coli* under ordinary conditions. Thus, even endogenous enzyme activities may need to be supplied to the cell via an extrachromosomal element such as a plasmid, cosmid and the like, as described in more detail elsewhere herein.

Surprisingly and advantageously, it was discovered that the 4HPA3H enzyme complex additionally catalyzes the conversion of tyrosine to L-dopa. More advantageously, L-dopa can in turn be converted into caffeic acid via the action of a TAL enzyme. Thus, in a particularly preferred embodiment, the novel pathway of the invention includes a TAL as an ammonia lyase and a 4HPA3H complex as an enzyme having C3H activity.

In a preferred embodiment, the novel biosynthetic pathway of the invention is thus capable of synthesizing caffeic acid by means of at least one, and preferably two pathways. When both pathways are present, they operate in parallel and constitute a dual pathway. In a first metabolic pathway, the precursor tyrosine is converted by TAL to p-coumaric acid which is converted by 4HPA3H to caffeic acid. In a second metabolic pathway, the precursor tyrosine is converted by 4HPA3H to L-dopa which is converted by TAL to caffeic acid. A schematic of these pathways is shown in FIG. 2B. Preferably and advantageously, these parallel pathways can operate simultaneously. In a particularly preferred embodiment, the 4HPA3H is an *E. coli* 4HPA3A enzyme complex and the TAL is a *Rhodobacter* TAL, preferably a *R. capsulatus* TAL. In an even more particularly preferred embodiment, the 4HPA3H is an *E. coli* 4HPA3H enzyme complex and the TAL is a *R. capsulatus* TAL.

Host Cells

The novel metabolic pathway described herein is introduced into a host cell using genetic engineering techniques. The term "cell" is meant to include any type of biological cell. The host cell can be a eukaryotic cell or a prokaryotic cell. Preferably, the host cell is a prokaryotic cell such as a bacterial cell; however single cell eukaryotes such as protists or yeasts are also useful as host cells. Host cells can be individually engineered to express one or more of the pathway enzymes as needed to complete the caffeic acid biosynthetic pathway as described herein; for example, they can be engineered to biosynthesize the starting material tyrosine if they do not natively produce it. Preferred host cells are microbial cells, preferably the cells of single-celled microbes such as bacterial cells or yeast cells. Examples of microbial cells that can be engineered to express the caffeic acid biosynthesis pathway as described herein, in addition to *E. coli*, include a wide variety of bacteria and yeast including members of the genera *Escherichia, Salmonella, Clostridium, Zymomonas, Pseudomonas, Bacillus, Rhodococcus, Alcaligenes, Klebsiella, Paenibacillus, Lactobacillus, Enterococcus, Arthrobacter, Brevibacterium, Corynebacterium Candida, Hansenula, Pichia* and *Saccharomyces*. Particularly preferred hosts include: *Escherichia coli, Bacillus subtilis Bacillus licheniformis, Alcaligenes eutrophus, Rhodococcus erythropolis, Paenibacillus macerans, Pseudomonas putida, Enterococcus faecium, Saccharomyces cerevisiae, Lactobacillus plantarum, Enterococcus gallinarium* and *Enterococcus faecalis*. In preferred embodiments, the host cell is a bacterial cell, such as an *E. coli* or *Streptomyces caeruleus* cell. In a particularly preferred embodiment, the host cell of the present invention is an *E. coli* cell.

The term "microbe" is used interchangeably with the term "microorganism" and means any microscopic organism existing as a single cell (unicellular), cell clusters, or multicellular relatively complex organisms. Microorganisms include, for example, bacteria, fungi, algae, protozoa, microscopic plants such as green algae, and microscopic animals such as rotifers and planarians. Preferably, a microbial host used in the present invention is single-celled. Notwithstanding the above preferences for bacterial and/or microbial cells, it should be understood that the metabolic pathway of the invention can be introduced without limitation into the cell of an animal, plant, insect, yeast, protozoan, bacterium, or archaebacterium.

A cell that has been genetically engineered to express one or more enzyme(s) described herein for caffeic acid biosynthesis may be referred to as a "host" cell, a "recombinant" cell, a "metabolically engineered" cell, a "genetically engineered" cell or simply an "engineered" cell. These and similar terms are used interchangeably. A genetically engineered cell contains one or more artificial sequences of nucleotides which have been created through standard molecular cloning techniques to bring together genetic material that is not natively found together. DNA sequences used in the construction of recombinant DNA molecules can originate from any species. For example, plant DNA may be joined to bacterial DNA, or human DNA may be joined with fungal DNA. Alternatively, DNA sequences that do not occur anywhere in nature may be created by the chemical synthesis of DNA, and incorporated into recombinant molecules. Proteins that result from the expression of recombinant DNA are often termed recombinant proteins. Examples of recombination are described in more detail below and may include inserting foreign polynucleotides (obtained from another species of cell) into a cell, inserting synthetic polynucleotides into a cell, or relocating or rearranging polynucleotides within a cell. Any form of recombination may be considered to be genetic engineering and therefore any recombinant cell may also be considered to be a genetically engineered cell.

Genetically engineered cells are also referred to as "metabolically engineered" cells when the genetic engineering modifies or alters one or more particular metabolic pathways so as to cause a change in metabolism. The goal of metabolic engineering is to improve the rate and conversion of a substrate into a desired product. General laboratory methods for introducing and expressing or overexpressing native and nonnative proteins such as enzymes in many different cell types (including bacteria, plants, and animals) are routine and well known in the art; see, e.g., Sambrook et al, *Molecular Cloning: A Laboratory Manual.*, Cold Spring Harbor Laboratory Press (1989), and *Methods for General and Molecular Bacteriology*, (eds. Gerhardt et al.) American Society for Microbiology, chapters 13-14 and 16-18 (1994).

Introduction of the Biosynthetic Pathway into a Cell

The introduction of the novel biosynthetic pathway of the invention into a cell involves expression or overexpression of one or more enzymes included in the novel pathway. An enzyme is "overexpressed" in a recombinant cell when the enzyme is expressed at a level higher than the level at which it is expressed in a comparable wild-type cell. In cells that do not express a particular endogenous enzyme, or in cells in which the enzyme is not endogenous (i.e., the enzyme is not native to the cell), any level of expression of that enzyme in the cell is deemed an "overexpression" of that enzyme for purposes of the present invention.

As will be appreciated by a person of skill in the art, overexpression of an enzyme can be achieved through a number of molecular biology techniques. For example, overexpression can be achieved by introducing into the host cell one or more copies of a polynucleotide encoding the desired enzyme. The polynucleotide encoding the desired enzyme may be endogenous or heterologous to the host cell. Preferably, the polynucleotide is introduced into the cell using a vector; however, naked DNA may also be used. The polynucleotide may be circular or linear, single-stranded or double stranded, and can be DNA, RNA, or any modification or combination thereof. The vector can be any molecule that may be used as a vehicle to transfer genetic material into a cell. Examples of vectors include plasmids, viral vectors, cosmids, and artificial chromosomes, without limitation. Examples of molecular biology techniques used to transfer nucleotide sequences into a microorganism include, without limitation, transfection, electroporation, transduction, and transformation. These methods are well known in the art. Insertion of a vector into a target cell is usually called transformation for bacterial cells and transfection for eukaryotic cells, however insertion of a viral vector is often called transduction. The terms transformation, transfection, and transduction, for the purpose of the instant invention, are used interchangeably herein. A polynucleotide which has been transferred into a cell via the use of a vector is often referred to as a transgene.

Preferably, the vector is an expression vector. An "expression vector" or "expression construct" is any vector that is used to introduce a specific polynucleotide into a target cell such that once the expression vector is inside the cell, the protein that is encoded by the polynucleotide is produced by the cellular transcription and translation machinery. Typically an expression vector includes regulatory sequences operably linked to the polynucleotide encoding the desired enzyme. Regulatory sequences are common to the person of the skill in the art and may include for example, an origin of replication, a promoter sequence, and/or an enhancer sequence. The polynucleotide encoding the desired enzyme can exist extrachromosomally or can be integrated into the host cell chromosomal DNA. Extrachromosomal DNA may be contained in cytoplasmic organelles, such as mitochondria (in most eukaryotes), and in chloroplasts and plastids (in plants). More typically, extrachromosomal DNA is maintained within the vector on which it was introduced into the host cell. In many instances, it may be beneficial to select a high copy number vector in order to maximize the expression of the enzyme. Optionally, the vector may further contain a selectable marker. Certain selectable markers may be used to confirm that the vector is present within the target cell. Other selectable markers may be used to further confirm that the vector and/or transgene has integrated into the host cell chromosomal DNA. The use of selectable markers is common in the art and the skilled person would understand and appreciate the many uses of selectable markers.

The genetically engineered cell of the invention expresses or overexpresses an ammonia lyase, preferably a tyrosine ammonia lyase (TAL). The host cell may or may not express a TAL endogenously. If it does not express an endogenous TAL, it is genetically engineered to express a TAL. In a preferred embodiment, the ammonia lyase is overexpressed; i.e., the genetically engineered cell expresses an ammonia lyase at a level higher than the level of ammonia lyase in a comparable wild-type cell. Where a cell does not express an ammonia lyase endogenously, any expression of the ammonia lyase is considered to be "overexpression." Determination of whether an ammonia lyase is expressed or overexpressed can easily be made by a person of skill in the art using a basic in vitro or in vivo enzyme assays. An exemplary in vitro ammonia lyase assay is described in Example 1 and in Xue et al. (J Ind Microbiol Biotechnol 2007, 34:599-604). Briefly, ammonia lyase activity can be measured and compared by obtaining crude enzyme extracts from an engineered cell and a comparable wild-type cell, subjecting a suitable substrate to each enzyme extract, and measuring the amount of product (i.e., p-coumaric acid and/or caffeic acid). Common methods for measuring the amount of the product may include, without limitation, chromatographic techniques such as size exclusion chromatography, separation based on charge or hydrophobicity, ion exchange chromatography, affinity chromatography, or liquid chromatography. The genetically engineered cell of the invention will yield a greater activity than a wild-type cell in such an assay. Additionally, or alternatively, the amount of ammonia lyase can be quantified and compared by obtaining protein extracts from the genetically engineered cell and a comparable wild-type cell and subjecting the extracts to any of number of protein quantification techniques which are well known in the art. Methods of protein quantification may include, without limitation, SDS-PAGE in combination with western blotting and mass spectrometry.

Figure 6A:
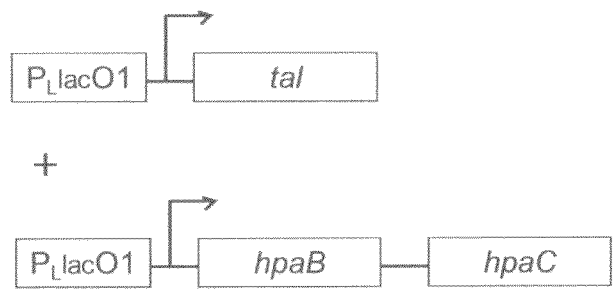
FIGS. 6A, 6B, and 6C show schematics of exemplary expression vectors. A, individual vectors, one expressing an ammonia lyase and the other expressing an enzyme having C3H activity; B, single vector expressing both ammonia lyase and C3H activity; C, tyrosine overproducer.

A gene encoding a TAL may be obtained from a suitable biological source, such as a bacterial cell, using standard molecular cloning techniques. For example, genes may be isolated using polymerase chain reaction (PCR) using primers designed by standard primer design software which is commonly used in the art. Exemplary primers for use in isolating TAL genes from R. capsulatus or R. sphaeroides can be found in Table 1. The cloned sequences are easily ligated into any standard expression vector by the skilled person. A schematic of an exemplary vector is shown in FIG. 6A (top).

In addition to overexpressing an ammonia lyase, the genetically engineered cell of the invention also expresses or overexpresses an enzyme having p-coumarate 3-hydroxylase (C3H) activity. In some embodiments, the genetically engineered cell may express a sufficient level of C3H activity, and overexpression of C3H activity may not be needed. However, in most instances, it is expected that the genetically engineered cell will overexpress C3H activity in order to achieve the desired level of caffeic acid production. Such a genetically engineered cell expresses an enzyme having C3H activity at a level higher than the level of C3H activity in the same comparable wild-type cell. This comparison is likewise easily made by a person of skill in the art using a basic in vitro or in vivo enzyme assays. An exemplary in vitro assay for detecting an enzyme having C3H activity is described in Example 1 and in Louie et al. (Louie et al., Biochemistry 2003, 42:7509-7517, which is incorporated by reference herein). Briefly, C3H activity can be measured and compared by obtaining crude enzyme extracts from a genetically engineered cell and a comparable wild-type cell, subjecting a suitable substrate to each enzyme extract, and measuring the amount of product (i.e., L-dopa and/or caffeic acid). An exemplary in vivo assay for detecting an enzyme having C3H activity is described in Example 1. Briefly, C3H activity can be measured and compared by incubating a suitable substrate (tyrosine and/or p-coumaric acid) with a cell culture and measuring the amount of product (i.e., L-dopa and/or caffeic acid). Common methods for measuring the amount of the product and common methods of protein quantification are well known in the art and are listed in brief above.

Any enzyme possessing C3H (p-coumarate 3-hydroxylase) activity can be utilized in the metabolic pathway of the invention. Preferably, the enzyme possessing C3H activity is soluble and not membrane-associated, allowing it to be expressed and active in a cytosolic environment such as inside a bacterial cell. Advantageously and surprisingly, as noted throughout, it was discovered that 4HPA3H (4-hydroxyphenylacetate 3-hydrolase) shows 3CH activity and can be utilized in the metabolic pathway of the invention. Thus, in a preferred embodiment, the enzyme having C3H activity which is expressed or overexpressed by the genetically engineered cell is 4HPA3H or a 4HPA3H complex. A 4HPA3H complex can contain two or more components that together provide enzymatic activity. The term "4HPA3H" when referred to herein means any enzyme or complex of enzyme that is a 4-hydroxyphenylacetate 3-hydrolase and which is additionally able to catalyse the conversion of p-coumaric acid to caffeic acid (i.e., which also has C3H activity). Any biological source of 3CH activity, in particular 4HPA3H, can be utilized. Examples of biological sources of 4HPA3H include, without limitation, *E. coli* (e.g., Xun et al., Appl Enviorn Microbiol 66(2):481-486), *Acinetobacter baumanni* (Phongsak et al., J. Biol. Chem. 287:26213-26222, 2012), *Thermus thermophilus* (Kim et al., J. Biol. Chem. 282:33107-33117, 2007), or *Ralstonia eutropha*. A convenient source of 3CH activity is the 4HPA3H complex derived from *E. coli*. The *E. coli* 4HPA3H complex is encoded by the hpaBC gene cluster and may be derived from *E. coli* using standard molecular cloning techniques. For example, genes may be isolated using PCR using primers designed by standard primer design software which is commonly used in the art. Exemplary primers for use in isolating the hpaBC gene complex from *E. coli* can be found in Table 2. The cloned sequences are easily ligated into any standard expression vector by the skilled person. A schematic of an exemplary vector is shown in FIG. 6A (bottom).

Figure 6B:

In one embodiment of the genetically engineered cell, separate, independent expression vectors are introduced into the host cell. A first expression vector is used to express an ammonia lyase, preferably a tyrosine ammonia lyase, and a second expression vector is used to express an enzyme or enzyme complex having C3H activity, such as 4HPA3H (FIG. 6A). In another embodiment, a single vector may be engineered to express both an ammonia lyase, preferably a tyrosine ammonia lyase, and an enzyme having C3H activity (FIG. 6B). When a single expression vector is used, each nucleotide sequence encoding a desired enzyme may be under the control of a single regulatory sequence or, alternatively, each nucleotide sequence encoding a desired enzyme may be under the control of independent regulatory sequences.

In one embodiment of the genetically engineered cell of the invention, the corresponding wild-type cell contains an endogenous enzyme having C3H activity, such as 4HPA3H. Preferred enzymes having C3H activity are described elsewhere herein. In this embodiment, the genetically engineered cell is optionally further engineered in modify the expression of the endogenous enzyme having C3H activity (or any other enzyme having C3H activity) so as to increase the level of C3H activity in the host cell. For example, the regulatory sequences can be modified (e.g., introduction of stronger regulatory sequences having a higher affinity for the transcriptional machinery). Alternatively, gene sequences which increase the translation of the mRNA can be introduced (e.g., introduction of processing sequencing such as introns).

The genetically engineered cell of the invention is optionally further engineered to overproduce tyrosine. Tyrosine overproducers are well-known to the art and they are preferred microorganisms as starting strains for the metabolic engineering. In *E. coli*, tyrosine biosynthesis is strictly controlled by several regulatory mechanisms. For example, two feedback inhibition-sensitive enzymes, chorismate mutase-prephenate dehydrogenase (CM-PDH, encoded by tyrA) and 3-deoxy-D-araibino-heptulosonate-7-phosphate synthase (DAHPS, encoded by aroG), have been identified Chavez-Bejar et al. (Appl Environ Microbiol 2008, 74:3284-3290). Tyrosine production can therefore be enhanced by metabolic engineering to eliminate feedback inhibition pathways that may otherwise be operating in the microorganism. Feedback inhibition resistant (fbr) variants of tyrA (tyrA$^{fbr}$) and aroG (aroG$^{fbr}$) can be engineered, for example, by introducing point mutations such as those that are described in Example 1, as well as by Heckman et al. (Nat Protoc 2007, 2:924-932) and Lutke-Eversloh et al. (Appl Environ Microbiol 2005, 71:7224-7228). Briefly, feedback inhibition resistant variant tyrA$^{fbr}$ can be generated by introducing Met-53-Ile and Ala-354-Val point mutations. Similarly, a feedback inhibition resistant variant aroG$^{fbr}$ can be generated by introducing an Asp-146-Asn point mutation. These point mutations can be readily generated using, for example, splicing and overlapping extension PCR. The tyrosine-overproducing cell is optionally further engineered to overexpress feedback inhibition resistant variants tyrA$^{fbr}$ and/or aroG$^{fbr}$. The tyrosine overproducing cell optionally overexpresses both variants tyrA$^{fbr}$ and aroG$^{fbr}$. Preferably, the tyrA$^{fbr}$ and aroG$^{fbr}$ can be derived from *E. coli*.

Figure 2A:
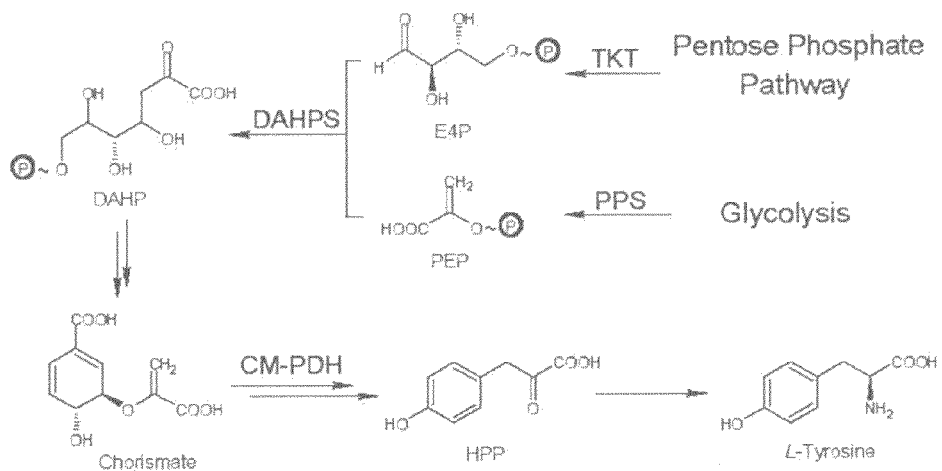
FIG. 2A shows a native tyrosine biosynthetic pathway in *E. coli*. Enzymes shown include phosphoenolpyruvate synthase (PPS), transketolase (TKT), chorismate mutase-prephenate dehydrogenase (CM-PDH), 3-deoxy-D-arabino-heptulosonate-7-phosphate synthase (DAHPS). Intermediates shown include D-erythrose-4-phosphate (E4P), phosphoenolpyruvate (PEP), 3-deoxy-D-arabino-heptulosonate-7-phosphate (DAHP), chorismate, and 4-hydroxyphenylpyruvate (HPP).
Figure 2B:
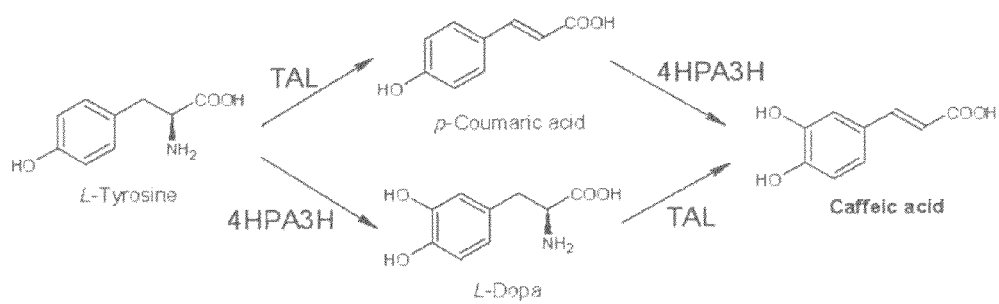
FIG. 2B shows an artificial dual pathway for caffeic acid biosynthesis from tyrosine. Enzymes shown include 4-hydroxyphenylacetate 3-hydroxylase (4HPA3H), and tyrosine ammonia lyase (TAL).
Figure 2C:
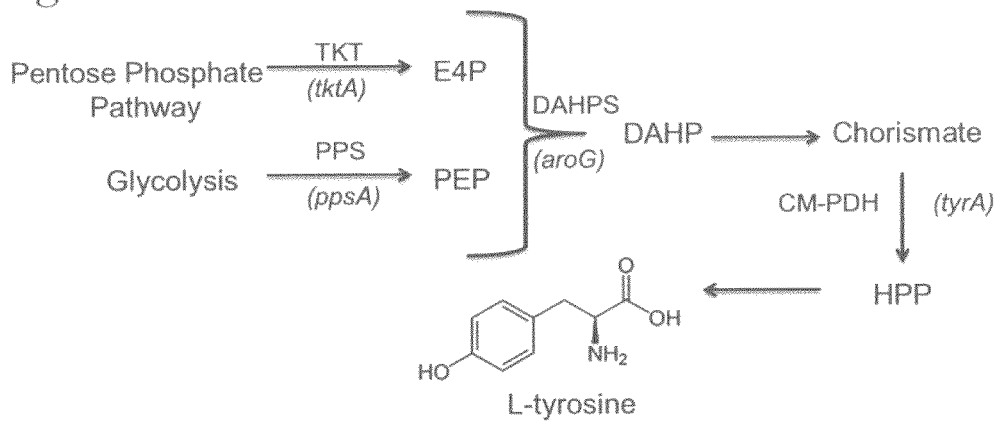
FIG. 2C shows a possible metabolic pathway optimization for a tyrosine overproducer. Enzymes shown include phosphoenolpyruvate synthase (PPS), transketolase (TKT), chorismate mutase-prephenate dehydrogenase (CM-PDH), 3-deoxy-D-arabino-heptulosonate-7-phosphate synthase (DAHPS). Intermediate products shown include D-erythrose-4-phosphate (E4P), phosphoenolpyruvate (PEP), 3-deoxy-D-arabino-heptulosonate-7-phosphate (DAHP), chorismate, and 4-hydroxyphenylpyruvate (HPP).

*E. coli* tyrosine biosynthesis is also regulated by the availability of intermediates erythrose-4-phosphate (E4P) and phosphoenolpyruvate (PEP) which are critical to tyrosine biosynthesis (see FIG. 2A). Thus, tyrosine production can be enhanced by metabolic engineering to divert carbon flow from other pathways and into the tyrosine biosynthesis pathway. Preferably, simple carbon sources are diverted into the tyrosine biosynthesis pathway. Exemplary simple carbon sources include glycerol, glucose, gluconate, acetate, xylose, sucrose, arabinose, mannose, and the like. Alternatively or additionally, the tyrosine overproducing cell is optionally further engineered to overexpress a PEP synthase (PPS) and/or a transketolase (TKT). A tyrosine overproducing cell optionally overexpresses either or both of PPS and TKT. Preferably, the PPS (encoded by the ppsA gene) and the TKT (encoded by the tktA gene) are derived from *E. coli*.

Figure 6C:

Any, some or all of these approaches may be utilized, alone or in any combination, to produce a tyrosine-overproducing host cell suitable for introduction of the novel metabolic pathway of the invention. In a particularly preferred embodiment, the tyrosine overproducing cell is engineered to both eliminate feedback inhibition pathways and divert carbon flow from other pathways into the tyrosine biosynthesis pathway. In one such embodiment, the engineered cell overexpresses tyrA$^{fbr}$, aroG$^{fbr}$, PPS, and TKT. These genes may be cloned into individual or multiple vectors or, advantageously, tyrA$^{fbr}$, aroG$^{fbr}$, PPS, and TKT may be consecutively cloned into a single expression vector. An exemplary expression vector containing each of tyrA$^{fbr}$, aroG$^{fbr}$, ppsA, and tktA is shown in FIG. 6C. Nucleic acid fragments containing any of the above mentioned genes can be isolated and inserted into vectors using standard molecular cloning techniques which are well known in the art. For example, the tyrA, aroG, ppsA, and tktA genes may be isolated using PCR using primers designed by standard primer design software which is commonly used in the art. Exemplary primers for use in isolating the tyrA, aroG, ppsA, and tktA genes from *E. coli* can be found in Table 2. Exemplary primers for use in splicing and overlapping extension PCR to generate the tyrA$^{fbr}$ and aroG$^{fbr}$ can also be found in Table 2.

Exemplary strains and vectors for use in the present invention are further set forth in Table 1 and discussed in Example 1.

An exemplary recombinant microorganism of the present invention is a bacterium, more preferably an *E. coli*, that overexpresses a TAL and overexpresses a 4HPA3H such that it is capable of synthesizing caffeic acid from the precursor tyrosine by means of a dual metabolic pathway which can advantageously operate simultaneously (FIG. 2B). A first metabolic pathway involves utilization of TAL to convert tyrosine to the metabolic intermediate p-coumaric acid, followed by utilization of 4HPA3H to convert p-coumaric acid into caffeic acid. A second metabolic pathway involves the same enzymes in reverse order: utilization of 4HPA3H to convert tyrosine to a different metabolic intermediate, L-dopa, followed by utilization of TAL to convert L-dopa to caffeic acid.

Production of Caffeic Acid and Caffeic Acid Derivatives and Downstream Metabolites The present invention further provides a method for producing caffeic acid, as well as caffeic acid derivatives and downstream metabolites, using the genetically engineered cell described herein. Briefly, and as described and illustrated in more detail elsewhere herein, the host cell is engineered to contain a novel biosynthetic pathway. Specifically, the host cell is engineered to overexpress an enzyme having ammonia lyase activity to convert tyrosine into the intermediate p-coumaric acid. The host cell is further engineered to overexpress an enzyme having C3H activity to catalyze the conversion of p-coumaric acid to caffeic acid. An enzyme having C3H activity native to E. coli, the 4HPA3H complex, also converts tyrosine to L-dopa. Surprisingly and advantageously, L-dopa can in turn be converted into caffeic acid via the action of a TAL enzyme. Thus, the instant invention provides a method to synthesize caffeic acid from the precursor tyrosine by means of at least one, and preferably two, parallel pathways.

The caffeic acid produced via the novel biosynthetic pathway can be isolated and optionally purified from any genetically engineered cell described herein. It can be isolated directly from the cells, or from the culture medium, for example, during an aerobic or anaerobic fermentation process. Isolation and/or purification can be accomplished using known methods. The present invention may also be extended by introducing additional selected metabolic enzymes to permit the microbial synthesis, production, isolation and/or purification of many other phenylpropanoids and polyphenols derived from caffeic acid. Examples of compounds that can be synthesized in addition to caffeic acid include flavonoids, stilbenes, coumarin, and the like. They find utility as nutraceuticals and pharmaceutical precursors, for example.

In the novel pathway for the production of caffeic acid, the amount of tyrosine in the genetically engineered cell may be limiting. Thus, in an alternative version of any embodiment described herein, the culture may be fed with additional tyrosine. However, a method that does not require the introduction of additional materials and instead enables the de novo synthesis of caffeic acid from simple carbon sources is envisioned by the present invention and is generally more desirable.

The genetically engineered cells of the invention can be cultured aerobically or anaerobically, or in a multiple phase fermentation that makes use of periods of anaerobic and aerobic fermentation. Preferably, the cells are cultured aerobically. Batch fermentation, continuous fermentation, or any other fermentation method may be used.

Importantly, the present invention permits a "total synthesis" or "de novo" biosynthesis of caffeic acid in the genetically engineered cell. In other words, it is not necessary to supply the genetically engineered cells with precursors or intermediates such as tyrosine or p-coumaric acid; caffeic acid can be produced using ordinary inexpensive carbon sources such as glucose, glycerol, gluconate, acetate and the like.

The present invention provides an elegant solution to the problem of producing that plant compound caffeic acid (and its derivatives and downstream metabolites) using a microbial system. It should be remembered, for example, that the biosynthesis of the plant compound caffeic acid in microorganisms such as bacteria and other prokaryotes is hindered by the fact that at least one of the enzymes involved in the plant biosynthetic pathway, p-coumarate 3-hydroxylase (C3H), is membrane bound. In the plant pathway, C3H catalyzes conversion of p-coumaric acid to caffeic acid. As noted above it was surprisingly discovered that an enzyme native to E. coli, the 4HPA3H complex, is also able to catalyze the conversion of p-coumaric acid to caffeic acid, thereby circumventing the need to attempt to express C3H in the metabolically engineered cell.

Additionally, in the plant pathway, p-coumaric acid is derived from the precursor phenylalanine. However, in at least one embodiment of the metabolic pathway provided by the present invention for microbes, phenylalanine is not the precursor; rather, the precursor is tyrosine, and the microorganism is metabolically engineered to express a tyrosine ammonia lyase (TAL) which converts tyrosine into the intermediate p-coumaric acid. The utilization of tyrosine as a starting point for the production of caffeic acid in place of phenylalanine is advantageous because there are many microbes that have been or can be engineered to overproduce tyrosine.

Surprisingly and advantageously, it was discovered that the 4HPA3H enzyme complex additionally catalyzes the conversion of tyrosine to L-dopa, and that L-dopa can in turn be converted into the target compound caffeic acid via the action of the TAL enzyme. This led to the development of the dual metabolic pathway as shown in FIG. 2B where these two enzymes are exploited for the microbial production of caffeic acid from both p-coumaric acid and L-dopa intermediates. As more carbon is pushed toward tyrosine via additional metabolic engineering of the microorganism, this dual pathway permits carbon to move through the tyrosine intermediate more efficiently and allows for even greater accumulations of caffeic acid.

The amount of tyrosine in the genetically engineered cell may be limiting, thus in an alternative version of any embodiment described herein, the cell is metabolically engineered to overproduce tyrosine. Tyrosine overproducers are well-known to the art and they are preferred cells as starting strains for the metabolic engineering. Tyrosine production can be enhanced by metabolic engineering to eliminate feedback inhibition pathways that may otherwise be operating in the cell, and/or by diverting carbon flow from other pathways into the tyrosine biosynthesis pathway(s). Metabolic engineering can be accomplished using plasmids that express one of more genes selected to produce the enzymatic activity or activities desired, and/or accomplished by direct genetic engineering on the genome of the microorganisms, using techniques well-known to the art. Exemplary means for increasing tyrosine production are described elsewhere herein.

The amount of 4-hydroxyphenylacetate 3-hydroxylase (4HPA3H) enzyme complex in the genetically engineered cell may be limiting, thus in an alternative version of any embodiment described herein, the cell is further metabolically engineered to overexpress one or more members 4HPA3H enzyme complex, such hpaB, hpaC or their counterparts.

The amount of tyrosine ammonia lyase (TAL) in the genetically engineered cell may be limiting, thus in an alternative version of any embodiment described herein, the amount (e.g., plasmid copy number) or biological source of TAL can be adjusted to produce more TAL enzyme activity.

Importantly, the present invention represents a "total synthesis" of caffeic acid in a genetically engineered cell, preferably a bacterial cell that can be readily employed in commercial production. It is not necessary to supply the microorganism with precursors or intermediates such as tyrosine or p-coumaric acid; caffeic acid can be produced using ordinary inexpensive carbon sources such as glucose, glycerol, gluconate, acetate and the like.

Exemplary biological sources of genes and enzymatic activities are described herein. For example, certain bacterial sources of tyrosine ammonia lyase (TAL) were used to construct the strains that exemplify the invention. However, it should be understood that what is important is that the metabolically engineered cell possess the designated enzymatic activities; the actual biological source of those activities is not important and can be determined by the skilled artisan based on availability or convenience.

In the preceding description, particular embodiments may be described in isolation for clarity. For example, several different cell types may be described in one section of the description, while several different enzymes or biological sources of enzymes may be described in another section of the description. It is expected that one of skill in the art will understand, that the description is explicitly intended to convey, that the various cell types described may be used in combination with the various enzymes and/or biological sources of enzymes, individually or collectively, in any reasonable conceivable combination to effect the biological production of caffeic acid. Unless it is otherwise expressly specified that the features of one particular embodiment are incompatible with the features of another embodiment, the invention is intended to encompass embodiments which include a combination of two or more compatible features described herein in connection, regardless of the textual position of the description of those embodiments within the document.

Moreover, it should be understood that preceding description is not intended to disclose every embodiment or every implementation of the present invention. The description more particularly exemplifies illustrative embodiments. For example, certain genes and enzymatic activities are described herein. However, it should be understood that what is important is that the genetically engineered cell possess the designated enzymatic activities; the actual biological source of those activities is not determinative or limiting and can be determined by the skilled artisan based on availability or convenience. In several places throughout the application, guidance is provided through lists of examples, which examples can be used in various combinations. In each instance, the recited list serves only as a representative group and should not be interpreted as an exclusive list.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Biosynthesis of Caffeic Acid in *Escherichia coli* Using its Endogenous Hydroxylase Complex Caffeic acid (3,4-dihydroxycinnamic acid) is a natural phenolic compound derived from the plant phenylpropanoid pathway. Caffeic acid and its phenethyl ester (CAPE) have attracted increasing attention for their various pharmaceutical properties and health-promoting effects. Nowadays, large-scale production of drugs or drug precursors via microbial approaches provides a promising alternative to chemical synthesis and extraction from plant sources. The development of processes that can enable the biosynthesis of these high-value metabolites from simple carbon sources is especially desirable.

We first identified that an *Escherichia coli* native hydroxylase complex previously characterized as the 4-hydroxyphenylacetate 3-hydroxylase (4HPA3H) was able to convert p-coumaric acid to caffeic acid efficiently. This critical enzymatic step, catalyzed in plants by a membrane-associated cytochrome P450 enzyme, p-coumarate 3-hydroxylase (C3H), is difficult to be functionally expressed in prokaryotic systems. Moreover, the performances of two tyrosine ammonia lyases (TALs) from *Rhodobacter* species were compared after overexpression in *E. coli*. The results indicated that the TAL from *R. capsulatus* (Rc) possesses higher activity towards both tyrosine and L-dopa. Based on these findings, we further designed a dual pathway leading from tyrosine to caffeic acid consisting of the enzymes 4HPA3H and RcTAL. This heterologous pathway extended *E. coli* native tyrosine biosynthesis machinery and was able to produce caffeic acid (12.1 mg/L) in minimal salt medium. Further improvement in production was accomplished by boosting tyrosine biosynthesis in *E. coli*, which involved the alleviation of tyrosine-induced feedback inhibition and carbon flux redirection. By utilizing tyrosine-overproducing strains as hosts, the production of several natural compounds such as L-dopa, flavonoids, and benzylisoquinoline alkaloids from simple carbon sources has already been achieved (Santos et al., Metab Eng 2011, 13:392-400; Nakagawa et al., Nat Commun 2011, 2:326; Munoz et al., J Ind Microbiol Biotechnol 2011, 38:1845-1852). Using these optimizations, the titer of caffeic acid reached 50.2 mg/L in shake flasks after 48-hour cultivation.

To summarize, we characterized the *E. coli* native 4-hydroxyphenlacetate 3-hydroxylase (4HPA3H) that was capable of hydroxylating p-coumaric acid and tyrosine in addition to its native substrate 4-hydroxyphenylacetic acid. Moreover, we found the TAL from *Rhodobacter capsulatus* was able to accept both tyrosine and L-dopa as substrates. Based on these findings, we designed a novel dual pathway leading from tyrosine to caffeic acid mediated by the enzymes 4HPA3H and TAL. As shown in FIG. 2B, native tyrosine biosynthesis can be extended by the introduction of the 4HPA3H and TAL, yielding L-dopa and p-coumaric acid, respectively. Then TAL further converts L-dopa to caffeic acid; while 4HPA3H converts p-coumaric acid into caffeic acid as well. Furthermore, by grafting this dual pathway into *E. coli*, we successfully achieved de novo biosynthesis of caffeic acid from simple, conventional sources of carbon.

We have therefore successfully established a novel pathway and constructed an *E. coli* strain for the production of caffeic acid. This work forms a basis for further improvement in production, as well as opens the possibility of microbial synthesis of more complex plant secondary metabolites derived from caffeic acid. In addition, we have identified that TAL is the rate-limiting enzyme in this pathway. Thus, the identification and utilization of more active TALs via bioprospecting and protein engineering approaches will further improvement of caffeic acid production. This work not only opens the route to the production of caffeic acid from simple carbon sources, but also paves the way to the microbial synthesis of many other phenylpropanoids derived from caffeic acid.

MATERIALS AND METHODS

Chemicals and Enzymes

The following commercially available chemicals and enzymes were used in this study: L-dopa (ACROS Organics); tyrosine (Sigma-Aldrich), caffeic acid (TCI), p-coumaric acid (MP Biochemicals), IPTG (Zymo Research Co.), restriction enzymes (NEB), Hot Start KOD Plus DNA polymerase (EMD Chemicals Inc.), Rapid DNA ligase Kit (Roche). All the enzymes were used according to the instructions provided by the manufacturers.

Molecular Biology Techniques

General molecular biology techniques and DNA manipulations were carried out according to the standard protocols (Sambrook et al., *Molecular cloning: a laboratory manual. 2nd edition*. NY: Cold Spring Harbor Laboratory; 1989). Deletion of kanamycin resistant gene from *E. coli* JW1316-1 was conducted using the method described by Kirill A. Datsenko and Barry L. Wanner (Datsenko and Wanner, Proc Natl Acad Sci USA 2000, 97:6640-6645). Host cells were transformed with the plasmids by electroporation (EPPENDORF Electroporator 2510, 1.8 kV when using 0.1 cm cuvettes).

TABLE 1

Strains and plasmids used in this study

| Plasmid or Strain | Relevant characteristics | Source |
|---|---|---|
| Plasmids | | |
| pZE12-luc | ColE1 ori; $Amp^R$; $P_L$lacO1; luc | 1 |
| pCS27 | p15A ori; $Kan^R$; $P_L$lacO1; MCS1 | 2 |
| pZE-RcTAL | From pZE12, $P_L$lacO1; tal(Rc) | This study |
| pZE-RsTAL | From pZE12, $P_L$lacO1; tal(Rs) | This study |
| pZE-EcHpaBC | From pZE12, $P_L$lacO1; hpaB(Ec)-hpaC(Ec) | This study |
| pZE-TH | From pZE12, $P_L$lacO1; tal(Rc)-hpaB(Ec)-hpaC(Ec) | This study |
| pCS-TPTA | From pCS27, $P_L$lacO1; $tyrA^{fbr}$-ppsA-tktA-$aroG^{fbr}$ | This study |
| Strains | | |
| XL1-Blue | recA1 endA1 gyrA96 thi-1 hsdR17 supE44 relA1 lac [F' proAB $lacI^qZ$ ΔM15 Tn10 ($Tet^R$)] | Stratagene |
| BW25113 | F-, Δ(araD-araB), ΔlacZ (::rrnB-3), λ-, rph-1, Δ(rhaD-rhaB), hsdR | Yale CGSC |
| JW1316-1 | BW25113, ΔtyrR::kan | Yale CGSC |
| YL-1 | BW25113, ΔtyrR::FRT (as JW1316-1, but $kan^R$ gene deleted) | This study |
| YL-2 | BW25113 harboring pZE-TH | This study |
| YL-3 | BW25113 harboring pCS-TPTA | This study |
| YL-4 | YL-1 harboring pCS-TPTA | This study |
| YL-5 | BW25113 harboring pZE-TH and pCS-TPTA | This study |
| YL-6 | YL-1 harboring pZE-TH and pCS-TPTA | This study |

1 Lutz and Bujard, Nucleic Acids Res 1997, 25:1203-1210
2 Shen and Liao, Metab Eng 2008, 10:312-320

Strains, Plasmids, Media, and Growth Conditions

*E. coli* XL1-Blue (Stratagene) was used for gene cloning and plasmid propagation. Wild type *E. coli* strain BW25113 (*E. coli* Genetic Resource Center) and its derivatives were employed for either enzyme assays or shake flask experiments. Plasmids pZE12-luc and pCS27 were used for gene over-expression in *E. coli* (Shen and Liao, Metab Eng 2008, 10:312-320; Lutz and Bujard, Nucleic Acids Res 1997, 25:1203-1210). The characteristics of all the strains and plasmids used in this study are described in Table 1. *E. coli* cells for gene cloning, plasmid propagation, and inoculum preparation were grown in Luria-Bertani (LB) medium at 37° C. The fermentation medium was modified M9 minimal salt medium containing (per liter): glycerol (10 g), glucose (2.5 g), $NH_4Cl$ (1 g), $Na_2HPO_4$ (6 g), $KH_2PO_4$ (3 g), NaCl (0.5 g), $MgSO_4.7H_2O$ (2 mmol), $CaCl_2.2H_2O$ (0.1 mmol), vitamin B1 (2.0 mg), $H_3BO_3$ (1.25 mg), $NaMoO_4.2H_2O$ (0.15 mg), $CoCl_2.6H_2O$ (0.7 mg), $CuSO_4.5H_2O$ (0.25 mg), $MnCl_2.4H_2O$ (1.6 mg), and $ZnSO_4.7H_2O$ (0.3 mg). For the strains carrying plasmids, 100 µg/ml of ampicillin, 50 µg/ml of kanamycin and/or 30 µg/ml of chloramphenicol were added if necessary. For all shake flask experiments, 200 µl overnight LB culture was inoculated into 10 ml fermentation medium and grown at 37° C. with shaking After $OD_{600}$ reached 0.4-0.5, IPTG was added into the cultures to a final concentration of 0.2 mM. Then the cultures were transferred to 30° C. in a gyratory shaker at 250 rpm. Samples were collected after 24 and 48 hours, and then analyzed by HPLC.

Construction of Plasmids

To construct pZE-RcTAL and pZE-RsTAL, the genes encoding RcTAL and RsTAL were amplified by high-fidelity polymerase chain reaction (PCR) from the genomic DNAs of *Rhodobacter capsulatus* and *Rhodobacter sphaeroides* using the primers listed in Table 2 (Xue et al., J Ind Microbiol Biotechnol 2007, 34:599-604). Amplified fragments and pZE12-luc were digested with KpnI and SphI, and then ligated with Rapid DNA ligase. To construct pZE-EcHpaBC, the gene cluster hpaBC was amplified from *E. coli* MG1655 genome directly. The amplified hpaBC fragment was inserted into pZE12-luc vector between KpnI and SphI as well. The pZE-TH was constructed by cloning the gene cluster hpaBC into the pZE-RcTAL using restriction enzymes SphI and XbaI. A ribosome binding site is located upstream of each gene to facilitate protein expression. The genes tyrA, aroG, ppsA, and tktA were all amplified from *E. coli* MG1655 genomic DNA. Point mutations were introduced to tyrA (Met-53-Ile and Ala-354-Val) and aroG (Asp-146-Asn) by splicing and overlapping extension PCR (SOE-PCR), generating $tyrA^{fbr}$ and $aroG^{fbr}$ (Heckman and Pease, Nat Protoc 2007, 2:924-932; Lutke-Eversloh and Stephanopoulos, Appl Environ Microbiol 2005, 71:7224-7228). The genes $tyrA^{fbr}$ and ppsA were first cloned into pCS27 simultaneously via three-piece ligation using restriction enzymes KpnI, NdeI, and SalI, generating the plasmid pCS-TP. Similarly, tktA and $aroG^{fbr}$ were then simultaneously inserted into pCS-TP using restriction enzymes XhoI, SphI, and HindIII resulting in pCS-TPTA.

TABLE 2

Primers used in this study

| Plasmid | Gene | Sequence (5'-3') | SEQ ID No: |
|---|---|---|---|
| pZE-RcTAL | tal(Rc) | F: gggaaaGGTACCatgctcgatgcaaccatcgg | 1 |
| | | R: gggaaaGCATGCtcatgccggggatcggc | 2 |
| pZE-RsTAL | tal(Rs) | F: gggaaaGGTACCatgctcgccatgagccc | 3 |
| | | R: gggaaaGCATGCtcagacgggagattgctgcaag | 4 |
| pZE-EcHpaBC | hpaBC(Ec) | F: gggaaaGGTACCatgaaaccagaagatttccgcgc | 5 |
| | | R: gggaaaGCATGCttaaatcgcagcttccatttccagc | 6 |
| pZE-TH | hpaBC(Ec) | F: gggaaaGCATGC*aggagat*ataccatgaaaccagaagatttccgcgccag | 7 |
| | | R: gggaaaTCTAGAttaaatcgcagcttccatttccagcatc | 8 |
| | tyrA/Met-53-Ile | F: gcgcgaggcatctattttggcctcgcgtcgtg | 9 |
| | | R: cacgacgcgaggccaaaatagatgcctcgcgc | 10 |
| | tyrA/Ala-354-Val | F: ctggttcggcgattacgtgcagcgttttcagagtg | 11 |
| | | R: cactctgaaaacgctgcacgtaatcgccgaaccag | 12 |
| | aroG/Asp- 146-Asn | F: gcaggtgagtttctcaacatgatcaccccac | 13 |
| | | R: gtgggtgatcatgttgagaaactcacctgc | 14 |
| pCS-TPTA | tyrA*fbr* | F: gggaaaGGTACCatggttgctgaattgaccgcattacg | 15 |
| | | R: gggaaaGTCGACgCATATGttactggcgattgtcattcgcctgac | 16 |
| pCS-TPTA | ppsA | F: gggaaaCATATG*aggagat*ataccatgtccaacaatggctcgtcac | 17 |
| | | R: gggaaaGTCGACttatttcttcagttcagccaggcttaac | 18 |
| pCS-TPTA | tktA | F: gggaaaCTCGAG*aggagat*ataccatgtcctcacgtaaagagcttgcc | 19 |
| | | R: gggaaaGCATGCttacagcagttcttttgctttcgcaac | 20 |
| pCS-TPTA | aroG*fbr* | F: gggaaaGCATGC*aggagat*ataccatgaattatcagaacgacgatttacgc | 21 |
| | | R: gggaaaAAGCTTttacccgcgacgcgcttttac | 22 |

Capital letters indicate restriction sites; italics indicate RBS

4HPA3H In Vitro Assay

The *E. coli* strain BW25113 carrying the plasmid pZE-EcHpaBC was pre-inoculated into LB liquid medium containing 100 µg/ml of ampicillin and grown at 37° C. overnight with shaking at 250 rpm. In the following day, 1 ml of preinoculum was added to 50 ml of fresh LB medium also containing 100 µg/ml of ampicillin. The culture was left to grow at 37° C. till $OD_{600}$ reached 0.6 and then induced with 0.5 mM IPTG. Protein expression was conducted at 30° C. for another 3 hours. The cells were harvested and resuspended in 2 ml of buffer A (20 mM $KH_2PO_4$, pH=7.0), and then lysed by French Press. The soluble fraction was collected by ultra-centrifugation and used as crude enzyme extract for the enzyme assay. Total protein concentration was estimated using the BCA kit (Pierce Chemicals). The total protein concentration of the crude extract is around 6172 µg/ml. The enzyme activity was assayed according to the protocol described by Tai et al. with a few modifications (Louie et al., Biochemistry 2003, 42:7509-7517). The 1 ml reaction system contained 2 mM NADH, 2 mM FAD, 2 mM substrate (tyrosine or p-coumaric acid) and 100 µl of crude enzyme extract in buffer A. The reaction was incubated at 30° C. for 1.5 minutes and terminated by adding 50 µl HCl (20%) to the 1 ml reaction system. The amount of products (L-dopa and caffeic acid, respectively) were measured and quantified by HPLC.

Whole-Cell Bioconversion by 4HPA3H

The *E. coli* strain BW25113 carrying the plasmid pZE-EcHpaBC was pre-inoculated into LB liquid medium containing 100 µg/ml of ampicillin and grown at 37° C. overnight with shaking at 250 rpm. Then 0.1 ml of preinoculum was added to 10 ml of fresh LB medium also containing 100 µg/ml of ampicillin. The culture was grown at 37° C. till $OD_{600}$ reached 0.6 and then induced with 0.5 mM IPTG for 3 hours. After that, 100 uL of p-coumaric acid (10 g/L) was added to reach a final concentration of 100 mg/L. Samples were collected at 3 hours and analyzed by HPLC.

4HPA3H In Vivo Assay

The pre-inoculum of *E. coli* strain BW25113 carrying pZE-EcHpaBC from an overnight culture was added in to 10 ml of LB medium (1:100 V/V) and grown at 37° C. IPTG was added to the cultures to a final concentration of 0.5 mM until $OD_{600}$ reached 0.6. The cultures were left at 30° C. for another 3 hours with shaking for protein expression till $OD_{600}$ reached 3.0 (approximately equivalent to 1 g/L cell). Then the cells were collected, washed, resuspended in 10 ml of NaCl (0.9%) solution. 1 mM substrate (tyrosine or p-coumaric acid) was added to the cell resuspensions at 30° C. Samples were collected after 1 and 2 hours, and then analyzed by HPLC.

Enzyme Assay of RcTAL and RsTAL

The crude enzyme extracts of RcTAL and RsTAL were prepared as described before (Xue et al., J Ind Microbiol Biotechnol 2007, 34:599-604). But the cells were resuspended in buffer B (50 mM, Tris-HCl, pH=8.5). The 1 ml reaction system contained 2 mM substrate (tyrosine or L-dopa) and 100 µl crude extract in buffer B. The reaction was incubated at 30° C. for 1.5 min and the amount of products (p-coumaric acid and caffeic acid, respectively) was measured by HPLC.

HPLC Analysis of Products

Tyrosine, L-dopa, p-coumaric acid, and caffeic acid generated in enzyme assays and fermentations were quantitatively analyzed by HPLC (Dionex Ultimate 3000) with a reverse-phase ZORBAX SB-C18 column and an Ultimate 3000 Photodiode Array Detector. The compounds were separated by elution with a methanol-water gradient (water containing 0.2% trifluoroacetic acid). The following gradient was used at a flow rate of 1 ml/minute: 10 to 50% methanol for 15 minutes, 50 to 10% methanol for 1 minute, and 10% methanol for an additional 4 minutes. Quantification for the four above-mentioned compounds was based on the peak areas of absorbance at 274, 280, 308 and 323 nm, respectively. The data shown in this study were generated from duplicate or triplicate independent experiments.

Results and Discussion

Plants and bacteria are very different in cell structure, physiology and genetics. One of the difficulties in reconstructing plant pathways in microbial systems is the availability of functional enzymes that are compatible with the specific microorganism. For the biosynthesis of caffeic acid in plants, two cytochrome P450-dependent monooxygenases are involved, which are C4H and C3H (Kim et al., Protein Expr Purif 2011, 79:149-155). Due to the requirement for anchorage on endoplasmic reticulum, functional expression of these plant P450-dependent enzymes were always problematic in bacterial systems (Kim et al., Protein Expr Purif 2011, 79:149-155; Leonard et al., Nat Chem Biol 2009, 5:292-300). Fortunately, TALs identified from various sources can catalyze the direct formation of p-coumaric acid from tyrosine bypassing the enzymatic step catalyzed by C4H (Xue et al., J Ind Microbiol Biotechnol 2007, 34:599-604), and thus, the need for a C4H was not obligatory. Nevertheless, the need for C3H still remains. Although an alternative microbial C3H was identified from *S. espanaensis*, its activity seems to be low, which limits its applications (Choi et al., J Ind Microbiol Biotechnol 2011, 38:1657-1665).

p-Coumaric Acid Hydroxylation by 4HPA3H

One of the most challenging steps in reconstructing plant phenylpropanoid pathway in *E. coli* is the 3-hydroxylation of p-coumaric acid, because all C3Hs identified in plants are cytochrome P450-dependent monooxygenases and are hard to be functionally expressed in bacterial systems (Kim et al., Protein Expr Purif 2011, 79:149-155). Therefore, the exploration of alternative enzymes compatible with *E. coli* is necessary. By examining *E. coli* native enzymes and pathways related to metabolism of aromatic compounds, we reasoned that the 4HPA3H complex encoded by the operon hpaBC involved in the 4-hydroxyphenylacetate (4-HPA) degradation may play the role of C3H (Louie et al., Biochemistry 2003, 42:7509-7517; Prieto et al., J Bacteriol 1993, 175:2162-2167). This enzyme complex can accept a broad range of substrates and has been applied to produce L-dopa and hydroxytyrosol from tyrosine and 4-tyrosol, respectively (Munoz et al., J Ind Microbiol Biotechnol 2011, 38:1845-1852; Louie et al., Biochemistry 2003, 42:7509-7517; Prieto et al., J Bacteriol 1993, 175:2162-2167; Liebgott et al., Res Microbiol 2009, 160:757-766). Because p-coumaric acid is similar to 4-HPA, tyrosine and 4-tyrosol in molecular structure (FIG. 3), we reasoned that the catalytic pocket of 4HPA3H should be able to accommodate p-coumaric acid as well.

To test this hypothesis, we first cloned hpaBC into a high-copy expression vector pZE12-luc. After over-expressing this enzyme complex in wild type *E. coli* BW25113, crude extract was prepared for in vitro enzyme assay. Our results indicate that 4HPA3H complex is capable of converting p-coumaric acid to caffeic acid in the presence of flavin adenine dinucleotide (FAD) and nicotinamide adenine dinucleotide hydride (NADH) (Table 3). Its specific activity toward p-coumaric acid ($5.37 \times 10^{-3}$ U/mg protein) is much higher than its activity toward tyrosine ($2.44 \times 10^{-3}$ U/mg protein).

TABLE 3

In vitro activity of 4HPA3H complex

| | Activity toward Substrate | | |
|---|---|---|---|
| Enzyme | A (tyrosine) ($10^{-3}$ U/mg protein) | B (p-coumaric acid) ($10^{-3}$ U/mg protein) | Ratio (A:B) |
| 4HPA3H | 2.44 ± 0.11 | 5.37 ± 0.31 | 0.45 |

One U (unit) is defined as the amount (1 μmole) of product formed per minute.

Figure 4:
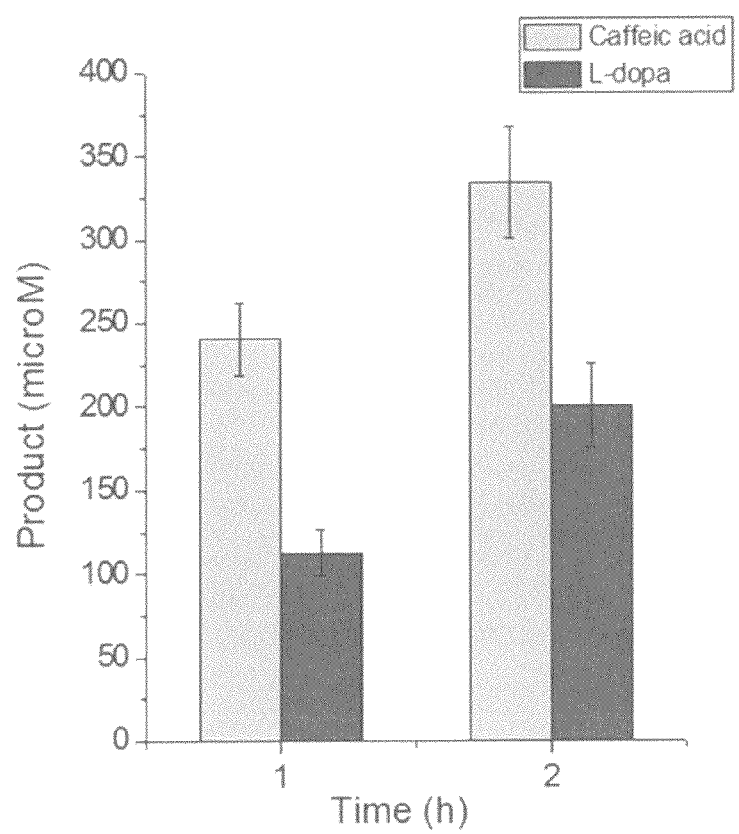
FIG. 4 shows in vivo enzyme activity of 4HPA3H complex toward tyrosine and p-coumaric acid. The grey and black bars show conversion efficiency and refer to the amount of caffeic acid and L-dopa produced, respectively.

Furthermore, we carried out whole-cell conversion studies which reflect the in vivo enzymatic activity. BW25113 harboring pZE-EcHpaBC was able to completely convert 100 mg/L p-coumaric acid to caffeic acid within 3 hours after the induction of isopropyl β-D-1-thiogalactopyranoside (IPTG), indicating the in vivo activity toward p-coumaric acid is high. Meanwhile, no caffeic acid was detected in the culture of the control strain (BW25113 harboring pZE12-luc) even after 20 hours. This phenomenon suggested that although hpaBC exists in the genome of *E. coli*, it is not natively expressed. Thus, over-expression of hpaBC is necessary to obtain adequate 4HPA3H activity. The result of in vivo enzyme assay showed that the highest conversion rates (within the first hour) from tyrosine to L-dopa and from p-coumaric acid to caffeic acid are 112.98 and 240.80 $\mu mol \cdot h^{-1} \cdot gDCW^{-1}$, respectively (FIG. 4). For both products, we did not observe obvious intracellular accumulation. Both in vitro and in vivo assay results indicate that p-coumaric acid is preferred by 4HPA3H. To our knowledge, this is the first report of the 4HPA3H activity toward p-coumaric acid.

Comparison of RcTAL and RsTAL

Previous studies reported that TALs from *R. capsulatus* (Rc) and *R. sphaeroides* (Rs) catalyze the deamination of tyrosine (Xue et al., J Ind Microbiol Biotechnol 2007, 34:599-604). In addition, RsTAL can also take L-dopa as a substrate (Noel et al., US Patent Application Pub. No. 2009/0011400 A1). But the activity of RcTAL toward L-dopa has not been investigated. To evaluate the performance of the two TALs in *E. coli*, we performed in vitro enzyme assays using crude extracts. The genes encoding the two TALs were cloned and expressed in *E. coli* using the plasmids pZE-RcTAL and pZE-RsTAL. Interestingly, both TALs slightly prefer L-dopa over their native substrate tyrosine. For RcTAL, the specific activities toward tyrosine and L-dopa were $0.93 \times 10^{-3}$ and $1.54 \times 10^{-3}$ U/mg protein, respectively. For RsTAL, the specific activities are $0.80 \times 10^{-3}$ and $1.14 \times 10^{-3}$ U/mg protein, respectively. The results indicated that RcTAL is slightly more active than RsTAL toward both substrates (Table 4). As a control, the crude extract of the wild-type *E. coli* carrying the blank vector did not exhibit any activity.

TABLE 4

Comparison of in vitro activity of RcTAL and RsTAL

| | Activity toward Substrate* | | |
|---|---|---|---|
| Enzyme | A (tyrosine) ($10^{-3}$ U/mg protein) | C (L-dopa) ($10^{-3}$ U/mg protein) | Ratio (A:C) |
| RcTAL | 0.93 ± 0.03 | 1.54 ± 0.05 | 0.60 |
| RsTAL | 0.80 ± 0.13 | 1.14 ± 0.03 | 0.70 |

*The crude extract of the wild-type *E. coli* did not show any TAL activity

Production of Caffeic Acid in *E. coli*

Figure 5:
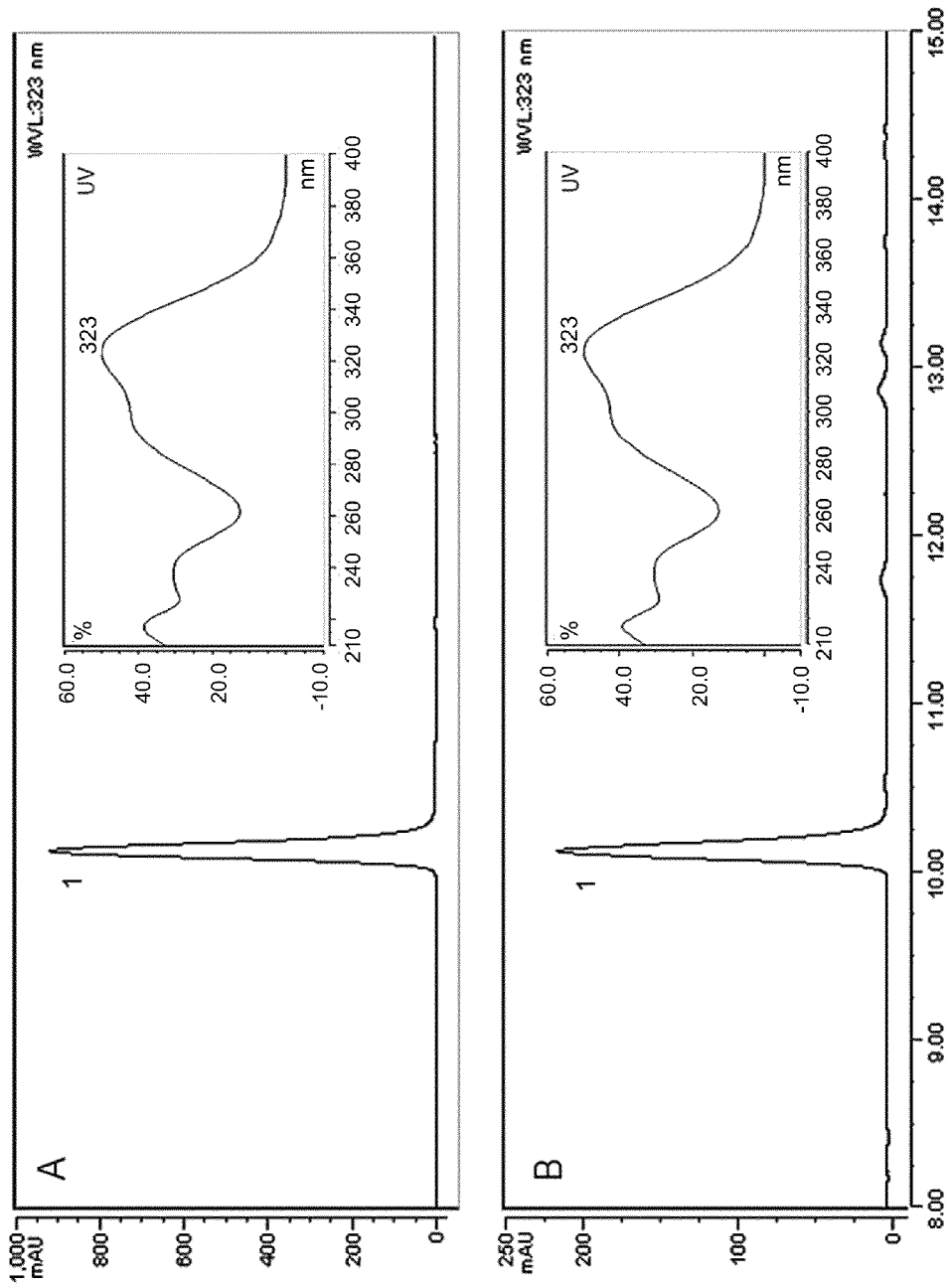
FIG. 5 shows an HPLC analysis of a caffeic acid standard (A) at 50 mg/L caffeic acid and an HPLC analysis of a sample of caffeic acid produced by engineered *E. coli* (B). Each sample was taken from the fermentation culture of YL-2 after 24 hours. Peak 1 corresponded to caffeic acid. The retention time was 10.1 minutes. UV absorbance profiles are shown beside the peaks.

Based on the activities of 4HPA3H and RcTAL, we proposed a novel dual pathway for caffeic acid biosynthesis from tyrosine (FIG. 2B). Because *E. coli* natively biosynthesizes tyrosine, it is expected that the introduction of RcTAL and 4HPA3H can result in the biosynthesis of caffeic acid by utilizing *E. coli* endogenous tyrosine. To achieve this goal, the genes encoding RcTAL and 4HPA3H were amplified and consecutively cloned into a high-copy-number plasmid pZE12-luc under the control of a strong IPTG-inducible promoter $P_L$lacO1, generating the plasmid pZE-TH. A ribosome binding site (RBS) was placed upstream of each gene. Strain YL-2 was developed by introducing pZE-TH into wild type *E. coli* strain BW25113 to test this pathway. The production of caffeic acid was carried out in shake flasks using modified M9 minimal salt medium as described in "Methods and Materials". High performance liquid chromatography (HPLC) analysis of the fermentation samples showed that the retention time (10.1 min) and UV profile of the product were identical to those of the caffeic acid standard, confirming that caffeic acid was produced (FIG. 5). The strain YL-2 was able to produce 11.1±1.1 mg/L caffeic acid after 24 hours, without obvious accumulation of intermediates including tyrosine, p-coumaric acid and L-dopa. 48-hour cultivation did not lead to a great increase in caffeic acid production (12.1±0.3 mg/L) (Table 5). However, L-dopa was accumulated at a concentration of 7.4±0.2 mg/L.

only slight improvement in tyrosine production compared to YL-3 in the first 24 hours. However, its advantage was demonstrated in the following 24 hours. These results are consistent with what were reported previously (Chavez-Bejar et al., Appl Environ Microbiol 2008, 74:3284-3290; Lutke-Eversloh and Stephanopoulos, Appl Microbiol Biotechnol 2007, 75:103-110).

TABLE 5

Production of caffeic acid and tyrosine by engineered *E. coli* strains

| | 24 hours | | | | 48 hours | | | |
|---|---|---|---|---|---|---|---|---|
| | Product (mg/L) | Intermediates (mg/L) | | | Product (mg/L) | Intermediates (mg/L) | | |
| Strain | caffeic acid | tyrosine | p-coumaric acid | L-dopa | caffeic acid | tyrosine | p-coumaric acid | L-dopa |
| YL-2 | 11.1 ± 1.1 | <0.2 | <0.2 | <0.2 | 12.1 ± 0.3 | <0.2 | <0.2 | 7.4 ± 0.2 |
| YL-2* | 20.2 ± 1.8 | <0.2 | <0.2 | 2.1 ± 0.3 | 21.5 ± 4.0 | <0.2 | <0.2 | 14.2 ± 1.7 |
| YL-3 | — | 188.9 ± 5.7 | — | — | — | 296.6 ± 1.0 | — | — |
| YL-4 | — | 218.6 ± 8.2 | — | — | — | 426.7 ± 4.9 | — | — |
| YL-5 | 30.5 ± 1.9 | 17.1 ± 1.8 | 2.9 ± 0.3 | 15.4 ± 1.7 | 50.2 ± 10.1 | 25.1 ± 2.5 | <0.2 | 75.3 ± 13.6 |

—: No production
*: addition of 100 mg/L tyrosine in the cultures

Construction of Tyrosine Overproducers

The addition of 100 mg/L tyrosine into the cultures of YL-2 resulted in a two-fold increase in caffeic acid production (Table 5), suggesting that tyrosine is a limiting precursor for caffeic acid biosynthesis. In wild-type *E. coli*, tyrosine biosynthesis is strictly controlled by several regulatory mechanisms. Two feedback inhibition-sensitive enzymes chorismate mutase-prephenate dehydrogenase (CM-PDH, encoded by tyrA) and 3-deoxy-D-arabino-heptulosonate-7-phosphate synthase (DAHPS, encoded by aroG) were identified as the major regulatory components in the tyrosine pathway (Chavez-Bejar et al., Appl Environ Microbiol 2008, 74:3284-3290). The feedback inhibition resistant (fbr) variants tyrA$^{fbr}$ and aroG$^{fbr}$ have already been developed and applied in tyrosine production (Chavez-Bejar et al., Appl Environ Microbiol 2008, 74:3284-3290; Lutke-Eversloh and Stephanopoulos, Appl Microbiol Biotechnol 2007, 75:103-110). In addition, the availability of erythrose-4-phosphate (E4P) and phosphoenolpyruvate (PEP) is extremely critical to tyrosine biosynthesis (FIG. 2A). Over-expression of PEP synthase (PPS, encoded by ppsA) and transketolase (TKT, encoded by tktA) was able to increase the availability of PEP and E4P, and redirect the carbon flux into the tyrosine pathway (Lutke-Eversloh and Stephanopoulos, Appl Microbiol Biotechnol 2007, 75:103-110). In this work, tyrA$^{fbr}$, ppsA, tktA and aroG$^{fbr}$ were consecutively cloned into a medium-copy-number plasmid pCS27 under the control of $P_L$lacO1 promoter as well, generating the plasmid pCS-TPTA. By introducing pCS-TPTA into wild type *E. coli* BW25113, we obtained a recombinant strain YL-3. Compared with wild type strain which produced little tyrosine, YL-3 was able to produce 296.6±1.0 mg/L tyrosine in 48 hours, which indicated that over-expression of the four enzymes was effective. Furthermore, the strain YL-1 (ΔtyrR) was also employed as the host to alleviate the tyrR-mediated regulation (Munoz et al., J Ind Microbiol Biotechnol 2011, 38:1845-1852). The introduction of pCS-TPTA into YL-1 (yielding strain YL-4) resulted in the accumulation of higher amount of tyrosine (426.7±4.9 mg/L in 48 h, Table 5). It should be noted that YL-4 exhibited Improvement of Caffeic Acid Production by Tyrosine Overproducing Strains Although YL-4 was able to produce higher amount of tyrosine, this tyrR-deleted strain seemed to be in conflict with pZE-derived plasmids for unknown reasons and did not express the enzymes 4HPA3H and RcTAL as well as expected. Only a trace amount of caffeic acid (<0.2 mg/L) and p-coumaric acid (<1 mg/L) but a large amount of tyrosine (>400 mg/L) were detected in the YL-6 (YL-1 harboring pZE-TH and pCS-TPTA) cultures. Thus, we employed wild type *E. coli* BW25113 as the parent strain. By transforming it with both pZE-TH and pCS-TPTA, we generated the strain YL-5. The titer of caffeic acid in the shake flask fermentation using YL-5 reached 50.2±10.1 mg/L after 48 h fermentation which is a 5-fold increase compared to YL-2. Moreover, we analyzed the intermediates accumulated in the culture. The presence of 25.1±2.5 mg/L tyrosine indicated that tyrosine availability is no longer the limiting factor for caffeic acid production in the strain YL-5. The accumulation of a large amount of L-dopa (75.3±13.6 mg/L) and a small amount of coumaric acid (<0.2 mg/L) suggested that RcTAL became into the rate-limiting step in this artificial pathway, especially after 24 h (Table 5).

CONCLUSIONS

We have successfully established a novel pathway and constructed an *E. coli* strain for the de novo production of caffeic acid via metabolic engineering approaches. We first identified that 4HPA3H can function as a p-coumarate 3-hydroxylase (C3H) which exhibited decent activity toward p-coumaric acid and tyrosine, thus gains great potential for metabolic engineering and biocatalysis applications. In addition, we compared the tyrosine ammonia lyases (TALs) from *R. capsulatus* (Rc) and *R. sphaeroides* (Rs) that are able to catalyze the deamination of both tyrosine and L-dopa. RcTAL exhibited higher activities toward both substrates. Then a dual pathway leading from tyrosine to caffeic acid was proposed and introduced into *E. coli*. The artificial pathway extended the native tyrosine pathway of *E. coli* and produced 12.1 mg/L of caffeic acid from simple carbon sources. Further improvement of production was accomplished via alleviating feedback inhibition and redirecting carbon flux into tyrosine biosynthesis. Finally, the titer of caffeic acid reached 50.2 mg/L in shake flasks after 48-hour cultivation.

This novel, metabolically engineered pathway obviated the use of two cytochrome P450-dependent monooxygenases (C4H and C3H) and achieved the de novo biosynthesis of caffeic acid, which opened the possibility of microbial synthesis of more complex plant secondary metabolites derived from caffeic acid. We have identified that RcTAL is the rate-limiting enzyme in the pathway once the tyrosine availability issue was solved. To meet the process metrics and avoid the accumulation of the intermediates (tyrosine and L-dopa), TALs having higher catalytic activity can be utilized, or identified de novo via bioprospecting and protein engineering approaches. In addition to the tyrosine overproducers we generated in this study, any of the strains currently employed to produce tyrosine in the amino acid industry are suitable as hosts for caffeic acid production. With proper process optimization, industrially relevant production can be achieved.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

What is claimed is:

1. A method for producing caffeic acid comprising:
   culturing a genetically engineered cell comprising p-coumarate 3-hydroxylase (C3H) enzyme activity, wherein said cell has been metabolically engineered to express or overexpress a tyrosine ammonia lyase (TAL) and to overexpress a 4-hydoxyphenylacetate 3-hydroxylase (4HPA3H) enzyme or enzyme complex, under conditions effective to produce caffeic acid; and
   isolating the caffeic acid from the cell or the culture medium.

2. The method of claim 1 further comprising supplying at least one carbon source selected from the group consisting of glycerol, glucose, gluconate, acetate, xylose, sucrose, arabinose, and mannose.

3. The method of claim 1 wherein the cell is a bacterial cell.

4. The method of claim 1 wherein the bacterial cell is an *Escherichia coli* cell.

5. The method of claim 1 wherein the culturing step is performed under aerobic conditions.

6. The method of claim 1 wherein the culturing step is performed under anaerobic conditions.

7. The method of claim 1 wherein the p-coumarate 3-hydroxylase (C3H) enzyme activity is provided by an endogenous 4-hydroxyphenylacetate 3-hydroxylase (4HPA3H) enzyme or enzyme complex.

8. The method of claim 1 wherein the genetically engineered cell further comprises a metabolic pathway for the biosynthesis of tyrosine.

9. The method of claim 8 wherein the genetically engineered cell has been further metabolically engineered to overproduce tyrosine compared to a wild-type cell.

10. The method of claim 1 wherein the genetically engineered cell has been further metabolically engineered to reduce or eliminate feedback inhibition of tyrosine biosynthesis.

11. The method of claim 9 wherein the genetically engineered cell has been further metabolically engineered to redirect carbon flow toward tyrosine biosynthesis.

12. The method of claim 10 wherein the genetically engineered cell has been further metabolically engineered to redirect carbon flow toward tyrosine biosynthesis.

13. The method of claim 1 wherein the genetically engineered cell comprises at least one vector operably encoding the tyrosine ammonia lyase (TAL).

14. The method of claim 13 wherein the genetically engineered cell comprises at least one vector operably encoding an enzyme having p-coumarate 3-hydroxylase (C3H) activity.

15. The method of claim 14 wherein a single vector encodes both the tyrosine ammonia lyase (TAL) and the enzyme having p-coumarate 3-hydroxylase (C3H) activity.

16. The method of claim 14 wherein the genetically engineered cell comprises a first vector encoding the tyrosine ammonia lyase (TAL) and a second vector encoding the enzyme having p-coumarate 3-hydroxylase (C3H) activity.

* * * * *